United States Patent [19]
Mylari et al.

[11] Patent Number: 5,866,578
[45] Date of Patent: *Feb. 2, 1999

[54] SUBSTITUTED PYRIMIDINES FOR CONTROL OF DIABETIC COMPLICATIONS

[75] Inventors: Banavara L. Mylari, Waterford; Peter J. Oates, Gales Ferry; Todd W.. Siegel, Clinton; William J. Zembrowski, Oakdale, all of Conn.

[73] Assignee: Pfizer Inc, New York, N.Y.

[*] Notice: The term of this patent shall not extend beyond the expiration date of Pat. No. 5,728,704.

[21] Appl. No.: 980,559

[22] Filed: Dec. 1, 1997

Related U.S. Application Data

[63] Continuation of Ser. No. 406,947, filed as PCT/US93/06446 Jul. 12, 1993 published as WO94/07867 Apr. 14, 1994, Pat. No. 5,728,704, which is a continuation-in-part of Ser. No. 952,222, Sep. 28, 1992, abandoned.

[51] Int. Cl.$^6$ ........................ A71K 31/505; C07D 401/04
[52] U.S. Cl. .......................... 514/256; 514/255; 544/242; 544/322; 544/329; 544/333
[58] Field of Search ............................ 514/256; 544/242, 544/322, 333, 329

[56] References Cited

U.S. PATENT DOCUMENTS 5,728,704  3/1998  Mylari et al. ........................... 514/256

Primary Examiner—Mukund J. Shah
Assistant Examiner—Pavanaram K. Sripada
Attorney, Agent, or Firm—Peter C. Richardson; Paul H. Ginsburg; Jolene W. Appleman

[57] ABSTRACT

This invention relates to methods of inhibiting sorbitol dehydrogenase, lowering fructose levels, and treating or preventing diabetic complications such as diabetic neuropathy, diabetic retinopathy, diabetic nephropathy, diabetic microangiopathy or diabetic macroangiopathy in a mammal using pyrimidine derivatives of the formula

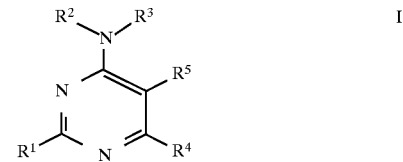

wherein $R^1$, $R^2$, $R^3$, $R^4$ and $R^5$ are defined as below, and to pharmaceutical compositions containing such derivatives. It also relates to certain novel substituted pyrimidines having the above formula. It also relates to mutual prodrugs of compounds of the formula I and aldose reductase inhibiting compounds, and to pharmaceutical compositions comprising a compound of the formula I and an aldose reductase inhibitor.

21 Claims, No Drawings

SUBSTITUTED PYRIMIDINES FOR CONTROL OF DIABETIC COMPLICATIONS

BACKGROUND OF THE INVENTION

This present application is a continuation application of U.S. patent application Ser. No. 08/406,947, filed Mar. 24, 1995 now U.S. Pat. No. 5,726,704 which was the National Stage Application of corresponding International Application Ser. No. PCT/US93/06446, filed Jul. 12, 1993 and published as WO 94/07867 on Apr. 14, 1994; which is a continuation in part of U.S. patent application Ser. No. 07/952,222, filed Sep. 28, 1992 now abandoned.

The present invention relates to novel pyrimidine derivatives and to the use of such derivatives and related compounds to inhibit sorbitol dehydrogenase, lower fructose levels, or treat or prevent diabetic complications such as diabetic neuropathy, diabetic retinopathy, diabetic nephropathy, diabetic microangiopathy and diabetic macroangiopathy in mammals. This invention also relates to pharmaceutical compositions containing such pyrimidine derivatives and related compounds.

S. Ao et al., *Metabolism*, 40, 77–87 (1991) have shown that significant functional improvement in the nerves of diabetic rats (based on nerve conduction velocity) occurs when nerve fructose levels are pharmacologically lowered, and that such improvement correlates more closely with the lowering of nerve fructose than the lowering of nerve sorbitol. Similar results were reported by N. E. Cameron and M. A. Cotter, *Diabetic Medicine*, 8, Suppl. 1, 35A–36A (1991). In both of these cases, lowering of nerve fructose was achieved using relatively high does of aldose reductase inhibitors, which inhibit the formation of sorbitol, a precursor of fructose, from glucose via the enzyme aldose reductase.

We have found that pyrimidine derivatives of the formula I, as defined below, and their pharmaceutically acceptable salts, lower fructose levels in the tissues of mammals affected by diabetes (e.g., nerve, kidney and retina tissue) and are useful in the treatment and prevention of the diabetic complications referred to above. These compounds, or their metabolites in vivo, are inhibitors of the enzyme sorbitol dehydrogenase, which catalyzes the oxidation of sorbitol to fructose.

SUMMARY OF THE INVENTION

The present invention also relates to the use of substituted pyrimidines of the formula I, as defined below, to treat or prevent diabetic complications in mammals, and to pharmaceutical compositions containing such pyrimidines.

Compounds of the formula I are those having the formula

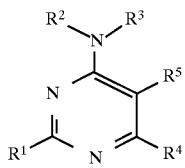

wherein $R^1$ is hydrogen, $CF_3$, $(C_1-C_6)$alkyl, $(C_1C_6)$alkyl-S—$(C_1-C_6)$alkyl, $(C_1-C_6)$alkyl-SO—$(C_1-C_6)$alkyl, $(C_1-C_6)$alkyl-SO$_2$—$(C_1-C_6)$alkyl, hydroxy-$(C_1-C_6)$alkyl, dihydroxy-$(C_1-C_6)$alkyl, $(C_1-C_6)$alkoxy, $(C_1-C_6)$alkoxycarbonyl-$(C_1-C_6)$alkyl, aryl selected from phenyl and naphthyl, aryl-$(C_1-C_6)$alkyl wherein the aryl moiety is selected from phenyl and naphthyl, $(C_1-C_6)$alkoxycarbonylaryl wherein the aryl moiety is selected from phenyl and naphthyl, aryl-$(C_1-C_6)$alkyl wherein the aryl moiety is selected from phenyl and naphthyl, aryl-$(C_1-C_6)$alkyloxy wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl, benzothiazolyl, benzofuranyl, and benzothienyl; heteroaryl-$(C_1-C_6)$alkyl wherein heteroaryl is defined as above, or heteroaryl-$(C_1-C_6)$alkyloxy wherein heteroaryl is defined as above, and wherein said aryl and heteroaryl groups, the aryl moieties of said aryl-$(C_1-C_6)$alkyl, $(C_1-C_6)$alkoxycarbonylaryl and aryl-$(C_1-C_6)$alkyloxy and the heteroaryl moiety of said heteroaryl-$(C_1-C_6)$alkyl may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl, hydroxy-$(C_1-C_6)$alkyl and trifluoromethyl;

or $R^1$ is a group of the formula

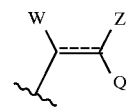

wherein the dotted line represents an optional double bond, W, Q and Z are independently selected from hydrogen, $(C_1-C_6)$alkyl and trifluoromethyl, phenyl, furyl, triazolyl, thiazolyl and thienyl, wherein said phenyl, furyl, triazolyl, thiazolyl and thienyl may optionally be substituted with one or more substituents independently selected from $(C_1-C_6)$alkyl, $(C_1-C_6)$alkoxy, trifluoromethyl and hydroxy;

or $R^1$ is a group of the formula

wherein $R^6$ is hydrogen, $(C_1-C_6)$alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents independently selected from chloro, bromo, nitro, trifluoromethyl, $(C_1-C_6)$alkoxy, —S—$(C_1-C_6)$alkyl, —SO—$(C_1-C_6)$alkyl and —SO$_2$—$(C_1-C_6)$alkyl;

or $R^1$ is a group of the formula

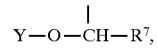

wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents independently selected from chloro, bromo, nitro, trifluoromethyl, $(C_1-C_6)$alkyl, $(C_1-C_6)$alkoxy, —S—$(C_1-C_6)$alkyl, —SO—$(C_1-C_6)$alkyl and —SO$_2$—$(C_1-C_6)$alkyl;

$R^2$ and $R^3$ are independently selected from hydrogen, $(C_1-C_6)$alkyl, phenyl and phenyl-$(C_1-C_4)$alkyl, wherein said phenyl and the phenyl moiety of said phenyl —$(C_1-C_4)$alkyl may optionally be substituted with one or more substituents independently selected from $(C_1-C_6)$alkyl, $(C_1-C_6)$alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents, independently selected from $(C_1-C_6)$alkyl, —$CONH_2$, —$SO_2NH_2$, N—$(C_1-C_4)$alkylsulfamoyl, N,N-di-$(C_1-C_4)$alkylsulfamoyl, $(C_1-C_6)$alkoxycarbonyl, N,N-di-$(C_1-C_4)$alkylcarbamoyl, N—$(C_1-C_4)$alkylcarbamoyl, N-phenylcarbamoyl, $(C_1-C_6)$alkylcarbonyl, phenylcarbonyl, $(C_1-C_6)$alkylsulfonyl, $(C_1-C_6)$alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents independently selected from $(C_1-C_4)$alkyl, $(C_1-C_4)$alkoxy, chloro, bromo, nitro, amino, cyano and trifluoromethyl;

$R^4$ is hydrogen, chloro, bromo, cyano, nitro, trifluoromethyl, amino, $(C_1-C_6)$alkyl, $(C_1-C_6)$hydroxyalkyl, $(C_1-C_6)$alkoxy, phenyl, naphthyl or furyl, wherein said phenyl, naphthyl and furyl may optionally be substituted with one or more substituents independently selected from chloro, bromo, trifluoromethyl, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl and hydroxy; and $R^5$ is hydrogen, $(C_1-C_6)$alkyl, $(C_1-C_6)$alkoxy, trifluoromethyl, $(C_1-C_6)$hydroxyalkyl, —S—$(C_1-C_6)$alkyl, —SO—$(C_1-C_6)$alkyl, —$SO_2$—$(C_1-C_6)$alkyl, phenyl or furyl, wherein said phenyl and furyl may optionally be substituted with one or more substituents independently selected from chloro, bromo, trifluoromethyl, $(C_1-C_6)$alkyl, $(C_1-C_6)$alkoxy, —SO—$(C_1-C_6)$alkyl, —$SO_2$—$(C_1-C_6)$alkyl and hydroxy.

Several of the substituted pyrimidines of formula I, as well as processes for preparing them, are referred to in European Patent Application 470,616A2, published Feb. 12, 1992 and European Patent Application 384,370A1, published Aug. 29, 1990. These references are incorporated herein by reference in their entirety.

More specifically, this invention relates to a pharmaceutical composition comprising a sorbitol dehydrogenase inhibiting effective amount of a compound of the formula I, or a pharmaceutically acceptable salt thereof, and a pharmaceutically acceptable carrier.

This invention also relates to a method of inhibiting the enzyme sorbitol dehydrogenase in a mammal, including a human, comprising administering to said mammal a sorbitol dehydrogenase inhibiting effective amount of a compound of the formula I, or a pharmaceutically acceptable salt thereof.

This invention also relates to a pharmaceutical composition comprising an amount of a compound of the formula I, or a pharmaceutically acceptable salt thereof, effective in lowering the level of fructose in one or more of the tissues of a mammal, including a human, that are affected by diabetes, and a pharmaceutically acceptable carrier.

This invention also relates to a method of lowering the level of fructose in one or more of the tissues of a mammal, including a human, that are affected by diabetes, comprising administering to said mammal a fructose lowering effective amount of a compound of the formula I, or a pharmaceutically acceptable salt thereof.

This invention also relates to a pharmaceutical composition comprising an amount of a compound of the formula I, or a pharmaceutically acceptable salt thereof, effective in treating or preventing a diabetic complication such as diabetic neuropathy, diabetic retinopathy, diabetic nephropathy, or diabetic microangiopathy or macroangiopathy in a mammal, including a human, and a pharmaceutically acceptable carrier.

This invention also relates to a method of treating or preventing a diabetic complication such as diabetic neuropathy, diabetic retinopathy, diabetic nephropathy, or diabetic microangiopathy or macroangiopathy in a mammal, including a human, comprising administering to said mammal an amount of a compound of the formula I, or a pharmaceutically acceptable salt thereof, effective in treating or preventing such complication.

This invention also relates to those compounds of the formula I wherein $R^1$ is $(C_1-C_6)$alkoxycarbonyl-$(C_1-C_6)$alkyl, $(C_1-C_6)$alkyl-S—$(C_1-C_6)$alkyl, $(C_1-C_6)$alkyl-SO—$(C_1-C_6)$alkyl, $(C_1-C_6)$alkyl-$SO_2$—$(C_1-C_6)$alkyl, dihydroxy-$(C_1-C_6)$alkyl, aryl, heteroaryl, heteroaryl-$(C_1-C_6)$alkyl, aryl-$(C_1-C_6)$alkyl, $(C_1-C_6)$alkoxycarbonylaryl, aryl-$(C_1-C_6)$alkyloxy or heteroaryl-$(C_1-C_6)$alkyloxy, wherein said aryl and the aryl moieties of said aryl-$(C_1-C_6)$alkyl, $(C_1-C_6)$alkoxycarbonylaryl, and aryl-$(C_1-C_6)$alkyloxy are independently selected from phenyl and naphthyl, and wherein said heteroaryl and the heteroaryl moieties of said heteroaryl-$(C_1-C_6)$alkyl and heteroaryl-$(C_1-C_6)$alkyloxy are independently selected from wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-$(C_1-C_6)$alkyl, aryl-$(C_1-C_6)$alkyl, $(C_1-C_6)$alkoxycarbonylaryl, aryl-$(C_1-C_6)$alkyloxy and heteroaryl-$(C_1-C_6)$alkyloxy may optionally be substituted with one or more substituents, preferably with one or two substituents, independently selected from chloro, bromo, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl, hydroxy-$(C_1-C_6)$alkyl and trifluoromethyl;

or $R^1$ is a group of the formula

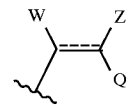

wherein the dotted line represents an optional double bond, W, Q and Z are independently selected from hydrogen, $(C_1-C_6)$alkyl and trifluoromethyl, phenyl, furyl, triazolyl, thiazolyl and thienyl, wherein said phenyl, furyl, triazolyl, thiazolyl and thienyl may optionally be substituted with one or more substituents, preferably with from zero to two substituents, independently selected from $(C_1-C_6)$alkyl, $(C_1-C_6)$alkoxy, trifluoromethyl and hydroxy;

or $R^1$ is a group of the formula

wherein $R^6$ is hydrogen, $(C_1-C_6)$alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents, preferably with from zero to two substituents, independently selected from chloro, bromo, nitro, trifluoromethyl, $(C_1-C_6)$alkoxy, —S—$(C_1-C_6)$alkyl, —SO—$(C_1-C_6)$alkyl and —SO$_2$—$(C_1-C_6)$alkyl;

or $R^1$ is a group of the formula

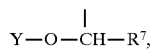

wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, $(C_1-C_6)$alkyl, $(C_1-C_6)$alkoxy, —S—$(C_1-C_6)$alkyl, —$(C_1-C_6)$alkyl, —SO$_2$—$(C_1-C_6)$alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents, preferably with from zero to two substituents, independently selected from chloro, bromo, nitro, trifluoromethyl, $(C_1-C_6)$alkyl, $(C_1-C_6)$alkoxy, —S—$(C_1-C_6)$alkyl, —SO—$(C_1-C_6)$alkyl and —SO$_2$—$(C_1-C_6)$alkyl.

These novel compounds are hereinafter referred to, collectively, as compounds of the formula IA. This invention also relates to the pharmaceutically acceptable acid addition and base salts of the novel compounds of formula IA.

This invention also relates to mutual prodrugs of a compound of the formula I and an aldose reductase inhibiting compound.

This invention also relates to compounds of the formula

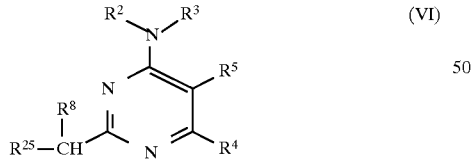

wherein $R^{25}$ is

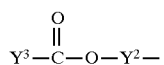

or

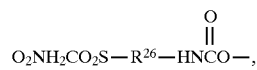

and $R^{26}$ is aryl selected from phenyl and naphthyl, wherein said aryl may optionally be substituted with one or more substituents, preferably with one or two substituents, independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl, hydroxy-$(C_1-C_6)$alkyl and trifluoromethyl;

$R^2$ and $R^3$ are independently selected from hydrogen, $(C_1-C_6)$alkyl, phenyl and phenyl-$(C_1-C_4)$alkyl, wherein said phenyl and the phenyl moiety of said phenyl —$(C_1-C_4)$alkyl may optionally be substituted with one or more substituents, preferably with from zero to two substituents, independently selected from $(C_1-C_6)$alkyl, $(C_1-C_6)$alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents independently selected from $(C_1-C_6)$alkyl, —CONH$_2$, —SO$_2$NH$_2$, N—$(C_1-C_4)$alkylsulfamoyl, N,N-di-$(C_1-C_4)$alkylsulfamoyl, $(C_1-C_6)$alkoxycarbonyl, N,N-di-$(C_1-C_4)$alkylcarbamoyl, N—$(C_1-C_4)$-alkylcarbamoyl, N-phenylcarbamoyl, $(C_1-C_6)$alkylcarbonyl, phenylcarbonyl, $(C_1-C_6)$alkylsulfonyl, $(C_1-C_6)$alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl and oxazolyl, and wherein the phenyl moieties of said phenylcarbonyl, N-phenylcarbamoyl, phenylcarbonyl and phenylsulfonyl may optionally be substituted with one or more substituents, preferably with from zero to two substituents, independently selected from $(C_1-C_4)$alkyl, $(C_1-C_4)$alkoxy, chloro, bromo, nitro, amino, cyano and trifluoromethyl;

$R^4$ is hydrogen, chloro, bromo, cyano, nitro, trifluoromethyl, amino, $(C_1-C_6)$alkyl, $(C_1-C_6)$hydroxyalkyl, $(C_1-C_6)$alkoxy, phenyl, naphthyl or furyl, wherein said phenyl, naphthyl and furyl may optionally be substituted with one or more substituents, preferably with from zero to two substituents, independently selected from chloro, bromo, trifluoromethyl, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl and hydroxy;

$R^5$ is hydrogen, $(C_1-C_6)$alkyl, $(C_1-C_6)$alkoxy, trifluoromethyl, $(C_1-C_6)$hydroxyalkyl, —S—$(C_1-C_6)$alkyl, —SO—$(C_1C_6)$alkyl, —SO$_2$—$(C_1-C_6)$alkyl, phenyl or furyl, wherein said phenyl and furyl may optionally be substituted with one or more substituents, preferably with from zero to two substituents, independently selected from chloro, bromo, trifluoromethyl, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl and hydroxy;

$R^8$ is hydrogen or $R^7$;

$R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl and trifluoromethyl, and Y is hydrogen, benzyl, acetyl, benzoyl, aryl selected from phenyl and naphthyl, or heteroaryl selected from furyl, thienyl, thiazolyl and oxazolyl, wherein said aryl and heteroaryl groups may optionally be substituted with one or more substituents, preferably with from zero to two substituents, independently selected from chloro, bromo, nitro, trifluoromethyl, $(C_1-C_6)$alkyl, $(C_1-C_6)$alkoxy, —S—$(C_1-C_6)$alkyl, —SO—$(C_1-C_6)$alkyl and —SO$_2$—$(C_1-C_6)$alkyl;

$Y^2$ is

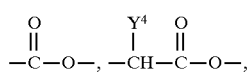

or $Y^2$ is absent (i.e., the carbon to which $R^8$ is attached is directly bonded to

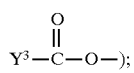

$Y^4$ is hydrogen or $(C_1-C_5)$alkyl; and
$Y^3$ is selected from the following groups:

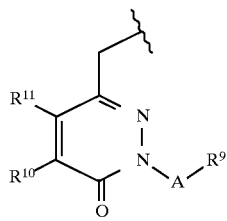
VII

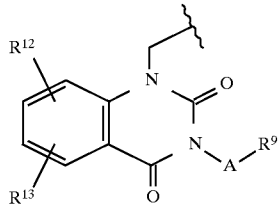
VIII

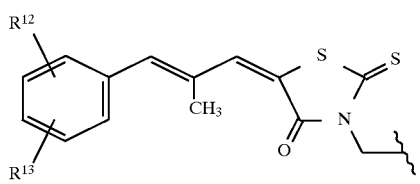
IX

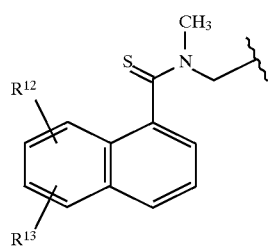
X

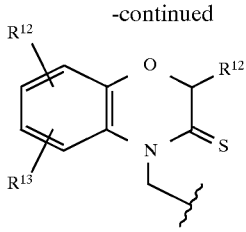
XI

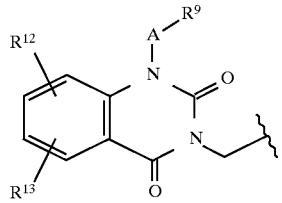
XII

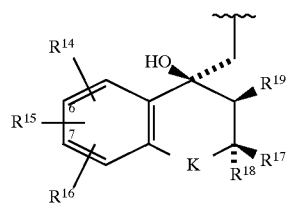
XIII

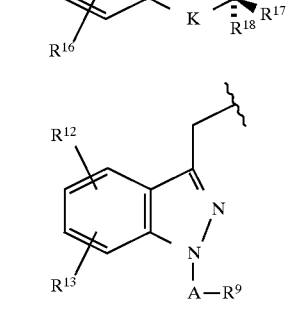
XIV and

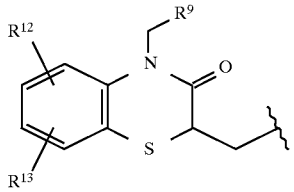
XIVA wherein A is $CH_2$, $CH_2CH_2$, $CH(CH_3)$ or

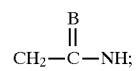

B is oxygen or sulfur;
$R^9$ is selected from phenyl, benzothiazol-2-yl, benzoxazol-2-yl, benzofuran-2-yl, benzothiophen-2-yl, thiazolopyridin-2-yl, oxazolopyridin-2-yl, 3-phenyl-1,2,4-oxadiazol-5-yl, and 5-phenyl-1,2,4-oxadiazol-3-yl, and $R^9$ may optionally be substituted with from one to three substituents independently selected from fluorine, chlorine, bromine, methyl, methylthio, methoxy, hydroxy and trifluoromethyl;
$R^{10}$ and $R^{11}$ are independently selected from hydrogen, fluorine, chlorine, bromine, $(C_1-C_4)$alkyl, $(C_1-C_4)$alkylthio, $(C_1-C_4)$alkoxy and trifluoromethyl;
or $R^{10}$ and $R^{11}$ together, with the carbons to which they are attached, form a group of the formula

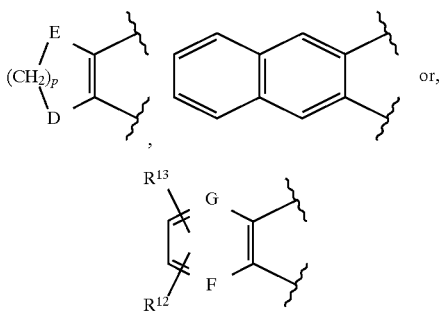

wherein p is 1 or 2; D and E are independently selected from —CH$_2$—, oxygen and sulfur, except that D and E cannot both be oxygen and cannot both be sulfur; R$^{12}$ and R$^{13}$ are independently selected from hydrogen, fluorine, chlorine, bromine, (C$_1$–C$_4$)alkyl, (C$_1$–C$_4$)alkylthio, (C$_1$–C$_4$)alkoxy and trifluoromethyl; and F and G are independently selected from —CH— and nitrogen;

R$^{12}$ and R$^{13}$ are independently selected from hydrogen, fluorine, chlorine, bromine, (C$_1$–C$_4$)alkyl, (C$_1$–C$_4$)alkylthio, (C$_1$–C$_4$)alkoxy and trifluoromethyl;

K is oxygen, sulfur, SO or SO$_2$;

R$^{14}$ is hydrogen, fluoro, chloro, bromo, methyl, nitro, cyano, methanesulfonyl or benzoyl;

R$^{15}$ is hydrogen, fluoro, chloro, bromo, carboxy, (C$_1$–C$_3$)alkyl, (C$_1$–C$_3$)alkoxy or benzyloxy;

R$^{16}$ is hydrogen, fluoro, chloro, bromo or (C$_1$–C$_3$)alkyl;

or R$^{15}$ and R$^{16}$, together with the carbon atoms to which they are attached, form a 7,8-benzo ring;

R$^{17}$ is (C$_1$–C$_4$)alkyl, trifluoromethyl or (CH$_2$)$_n$Ar, wherein n is 0, 1 or 2 and Ar is phenyl optionally substituted with one or two substituents independently selected from methoxy, fluoro, chloro and bromo;

R$^{18}$ is hydrogen, methyl or ethyl;

or R$^{17}$ and R$^{18}$, together with the carbon to which they are attached, form a saturated 4 or 5 membered carbocyclic spiro ring; and R$^{19}$ is hydrogen or methyl;

with the proviso that: (a) when K is other than oxygen, R$^{14}$ is fluoro, chloro, cyano or nitro, and R$^{15}$ and R$^{16}$ do not form a 7,8-benzo ring; and (b) when K is other than oxygen or R$^{17}$ is other than methyl, ethyl or trifluoromethyl, both R$^{18}$ and R$^{19}$ are hydrogen; and (c) when Y$^3$ is a group of the formula XIVA, R$^9$ is benzothiazol-2-yl or substituted benzothiazol-2-yl;

and the pharmaceutically acceptable salts of such compounds.

Compounds of the formula

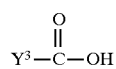

wherein Y$^3$ is one of the above groups VII to XIV are known aldose reductase inhibitors. Compounds of the formula VI wherein R$^{25}$ is

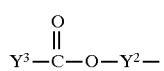

are conjugates and mutual prodrugs of such aldose reductase inhibitors and the pharmaceutically active compounds of the formula I wherein R$^1$ is —CH$_2$OH, —CHR$^7$OH or hydroxy-(C$_1$–C$_6$)alkyl. As mutual prodrugs, they are expected to release in vivo both pharmaceutically active agents—a compound of the formula I wherein R$^1$ is —CH$_2$OH, —CHR$^7$OH or hydroxy-(C$_1$–C$_6$)alkyl and an aldose reductase inhibitor of the formula

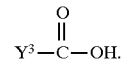

Compounds of the formula O$_2$N—CH$_2$—SO$_2$—R$^{26}$—NH$_2$, wherein R$^{26}$ is defined as above, are also known aldose reductase inhibitors. Compounds of the formula VI wherein R$^{25}$ is

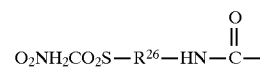

are conjugates and mutual prodrugs of such aldose reductase inhibitors and the pharmaceutically active compounds of the formula I wherein R$^1$ is —CH$_2$OH, —CHR$^7$OH or hydroxy-(C$_1$–C$_6$)alkyl. As mutual prodrugs, they are expected to release in vivo both pharmaceutically active agents—a compound of the formula I wherein R$^1$ is —CH$_2$OH, —CHR$^7$OH or hydroxy-(C$_1$–C$_6$)alkyl and an aldose reductase inhibitor of the formula O$_2$N—CH$_2$—SO$_2$—R$^{26}$—NH$_2$.

Preferred embodiments of this invention include those compounds of the formula VI, and pharmaceutically acceptable salts thereof, wherein R$^{25}$ is

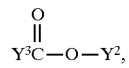

Y$^2$ is not absent and: (a) Y$^3$ is a group of the formula VII, R$^9$ is phenyl, substituted phenyl, benzothiazol-2-yl or benzoxazol-2-yl, A is —CH$_2$—, and R$^{10}$ and R$^{11}$ are either both methyl or they form, together with the carbons to which they are attached, a group of the formula

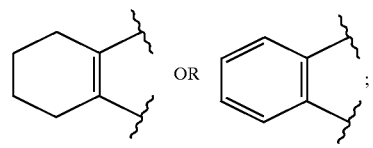

(b) Y$^3$ is a group of the formula VIII, R$^9$ is phenyl, substituted phenyl, benzothiazol-2-yl or benzoxazol-2-yl, A is —CH$_2$—, and R$^{12}$ and R$^{13}$ are independently selected from bromo and chloro; (c) Y$^3$ is a group of the formula IX and each of R$^{12}$ and R$^{13}$ is hydrogen; (d) Y$^3$ is a group of the formula X and R$^{12}$ and R$^{13}$ are independently selected from (C$_1$–C$_6$)alkoxy and trifluoromethyl; (e) Y$^3$ is a group of the formula XI and R$^{12}$ and R$^{13}$ are independently selected from (C$_1$–C$_6$)alkyl; (f) Y$^3$ is a group of the formula XII, R$^9$ is phenyl, substituted phenyl or benzothiazol-2-yl, A is —CH$_2$— and R$^{12}$ and R$^{13}$ are independently selected from chloro and bromo; or (g) Y$^3$ is a group of the formula XIII, each of R$^{14}$ and R$^{19}$ is hydrogen, each of R$^{17}$ and R$^{18}$ is methyl, R$^{15}$ is 6-chloro or 6-fluoro and R$^{16}$ is 7-chloro or 7-fluoro.

Preferred embodiments of this invention also include those compounds of the formula VI that are mutual prodrugs of a compound of the formula I and an aldose reductase inhibitor of the formula

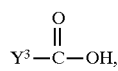

wherein such aldose reductase inhibitor is selected from:
3,4-dihydro-4-oxo-3-[[(5-trifluoromethyl)-2-benzothiazolyl]-methyl]-1-phthalazineacetic acid;
3,4-dihydro-4-oxo-3-[[(5,7-difluoro)-2-benzothiazolyl]-methyl]-1-phthalazineacetic acid;
3,4-dihydro-4-oxo-3-[[(5,7-dichloro)-2-benzothiazolyl]-methyl]-1-phthalazineacetic acid;
2-[4-(4,5,7-trifluorobenzothiazol-2-yl)methyl-3,4-dihydro-3-oxo-2H-1,4-benzothiazin-2-yl] acetic acid;
[4,5-dimethyl-6-oxo-1-(5-trifluoromethyl-benzothiazolylmethyl)-1,6-dihydro-pyridazin-3-yl]-acetic acid;
[4,5-dimethyl-6-oxo-1-(5,7-difluoro-benzothiazolylmethyl)-1,6-dihydro-pyridazin-3-yl]-acetic acid;
[4,5-dimethyl-6-oxo-1-(5,7-dichlorobenzothiazol-2-ylmethyl)-1,6-dihydro-pyridazin-3-yl]-acetic acid;
4-oxo-3[[(5-trifluoromethyl)-benzothiazol-2-ylmethyl]3,4,5,6,7,8-hexahydro-phthalazin-1-yl]-acetic acid;
4-oxo-3-[[(5,7-difluoro)-benzothiazol-2-ylmethyl]-3,4,5,6,7,8-hexahydro-phthalazin-1-yl]-acetic acid;
4-oxo-3-[[(5,7-dichloro)-benzothiazol-2-ylmethyl]-3,4,5,6,7,8-hexahydro-phthalazin-1-yl]-acetic acid;
N-[[5-trifluoromethyl)-6-methoxy-1-naphthalenyl]thioxomethyl]-N-methylglycine;
3,4-dihydro-4-oxo-3-(4-bromo-2-fluorobenzyl)-1-phthalazineacetic acid;
(Z)-3-(carboxymethyl-[(2E)-methylphenylpropenylidene]-rhodanine;
2-[3-(4-bromo-2-fluorobenzyl)-7-chloro-1,2,3,4-tetrahydro-2,4-dioxo-1-quinazolinyl]-acetic acid;
2R,4R-6,7-dichloro-4-hydroxy-2-methylchroman-4-acetic acid;
2R,4R-7-chloro-6-fluoro-4-hydroxy-2-methylchroman-4-acetic acid; and
3,4-dihydro-2,8-diisopropyl-3-oxo-2H-1,4-benzoxazine-4-acetic acid.

This invention also relates to a pharmaceutical composition comprising: (a) an amount of a mutual prodrug of a compound of the formula I and an aldose reductase inhibiting compound, or a pharmaceutically acceptable salt of such a prodrug, effective in lowering the level of fructose in one or more of the tissues of a mammal, including a human, that are affected by diabetes; and (b) a pharmaceutically acceptable carrier.

This invention also relates to a method of lowering the level of fructose in one or more of the tissues of a mammal, including a human, that are affected by diabetes, comprising administering to said mammal a fructose lowering effective amount of a mutual prodrug of a compound of the formula I and an aldose reductase inhibiting compound, or a pharmaceutically acceptable salt of such a prodrug.

This invention also relates to a pharmaceutical composition comprising: (a) an amount of a mutual prodrug of a compound of the formula I and an aldose reductase inhibiting compound, or a pharmaceutically acceptable salt of such a prodrug, effective in treating or preventing a diabetic complication such as diabetic neuropathy, diabetic retinopathy, diabetic nephropathy, or diabetic microangiopathy or macroangiopathy in a mammal, including a human; and (b) a pharmaceutically acceptable carrier.

This invention also relates to a method of treating or preventing a diabetic complication such as diabetic neuropathy, diabetic retinopathy, diabetic nephropathy, or diabetic microangiopathy or macroangiopathy in a mammal, including a human, comprising administering to said mammal an amount of a mutual prodrug of a compound of the formula I and an aldose reductase inhibiting compound, or a pharmaceutically acceptable salt of such a prodrug, effective in treating or preventing such complication.

This invention relates to a pharmaceutical composition comprising an amount of a compound of the formula VI, or a pharmaceutically acceptable salt thereof, effective in lowering the level of fructose in one or more of the tissues of a mammal, including a human, that are affected by diabetes, and a pharmaceutically acceptable carrier.

This invention also relates to a method of lowering the level of fructose in one or more of the tissues of a mammal, including a human, that are affected by diabetes, comprising administering to said mammal a fructose lowering effective amount of a compound of the formula VI, or a pharmaceutically acceptable salt thereof.

This invention also relates to a pharmaceutical composition comprising an amount of a compound of the formula VI, or a pharmaceutically acceptable salt thereof, effective in treating or preventing a diabetic complication such as diabetic neuropathy, diabetic retinopathy, diabetic nephropathy, or diabetic microangiopathy or macroangiopathy in a mammal, including a human, and a pharmaceutically acceptable carrier.

This invention also relates to a method of treating or preventing a diabetic complication such as diabetic neuropathy, diabetic retinopathy, diabetic nephropathy, or diabetic microangiopathy or macroangiopathy in a mammal, including a human, comprising administering to said mammal an amount of a compound of the formula VI, or a pharmaceutically acceptable salt thereof, effective in treating or preventing such complication.

Compounds of the formulae XV–XIX, which are defined below, and their pharmaceutically acceptable salts, are also known compounds that exhibit activity as aldose reductase inhibitors. These compounds have the following structures:

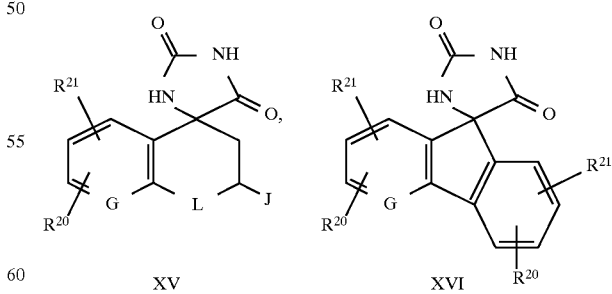

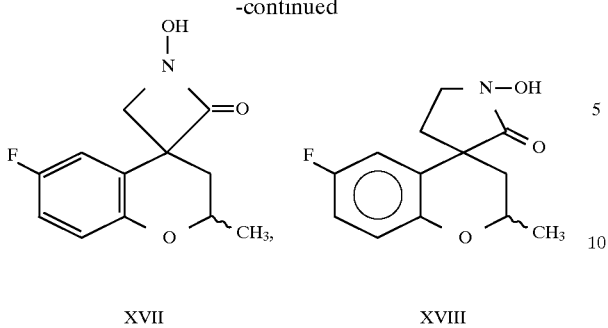

XVII        XVIII and

MSO$_2$CH$_2$NO$_2$

XIX wherein L is oxygen, CH$_2$ sulfur or

J is hydrogen, methyl or —CNH$_2$;

G is CH or N;

$R^{20}$ and $R^{21}$ are independently selected from hydrogen, fluorine, chlorine, (C$_1$–C$_6$)alkyl, (C$_1$–C$_6$)alkoxy, —S—(C$_1$–C$_6$)alkyl, —SO—(C$_1$—C$_6$)alkyl or —SO$_2$—(C$_1$C$_6$)alkyl;

M is phenyl, naphthyl or a heteroaryl group selected from furan, morpholine, pyrrolidine, tetrahydroisoquinoline, thiophene, thiazole, oxazole, benzofuran, benzothiophene, benzothiazole, benzoxazole and indole, wherein said phenyl, naphthyl and heteroaryl groups may optionally be substituted with up to three substituents independently selected from chloro, fluoro, bromo, cyano, nitro, hydroxy, carboxy, amino (C$_1$–C$_6$) alkylamino, (C$_1$–C$_6$)dialkylamino, (C$_1$–C$_6$) alkanoylamino, (C$_1$–C$_6$)alkanoyl, (C$_1$–C$_6$)alkyl, (C$_2$–C$_6$)alkenyl, (C$_3$–C$_6$)alkenyloxy, fluoro-(C$_1$–C$_6$) alkyl, (C$_1$–C$_6$)alkoxy, fluoro-(C$_1$–C$_4$)alkoxy, (C$_1$–C$_6$) hydroxyalkyl, carbamoyl, (C$_1$–C$_7$)alkylcarbamoyl, (C$_1$–C$_7$)dialkylcarbamoyl, sulfamoyl, (C$_1$–C$_6$) alkysulfamoyl, (C$_1$–C$_6$)dialkylsulfamoyl, (C$_1$–C$_6$) alkoxycarbonyl, (C$_1$–C$_4$)alkylenedioxy,(C$_1$–C$_6$) alkanesulfonamido, —S—(C$_1$–C$_6$)alkyl, —SO—(C$_1$–C$_6$)alkyl, —SO$_2$—(C$_1$–C$_6$)alkyl, phenyl, phenoxy, benzyloxy, benzyloxycarbonyl, benzamido, and benzenesulfonamido, and wherein said phenyl and the phenyl moieties of said phenoxy, benzyloxy, benzyloxycarbonyl, benzamido and benzenesulfonamido may optionally be substituted with a substituent selected from chlorine, fluorine, (C$_1$–C$_4$)alkyl (C$_1$–C$_4$) alkoxy and

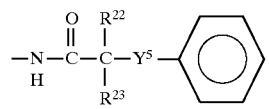

wherein $Y^5$ is oxygen or sulfur, or $Y^5$ is absent (i.e., the phenyl ring is bonded to the carbon to which $R^{22}$ and $R^{23}$ are attached), and $R^{22}$ and $R^{23}$ are independently selected from hydrogen and (C$_1$–C$_4$)alkyl, and the phenyl moiety to which the —NHCOC($R^{22}$)($R^{23}$)—$Y^5$— sidechain is attached may optionally be substituted with from one to three substituents independently selected from hydrogen, halo, trifluoromethyl, nitro, cyano, (C$_1$–C$_4$)alkyl, (C$_1$–C$_4$)alkoxy and (C$_1$–C$_4$)alkanoyl, or any adjacent pair of substituents may form, together with the carbons to which they are attached, a benzo ring which may optionally be substituted with a substituent independently selected from halo, (C$_1$–C$_4$)alkyl and (C$_1$–C$_4$)alkoxy;

with the proviso that: (a) when J is

G is CH and L is oxygen; and (b) M is not 2-carboxyphenyl.

This invention also relates to a pharmaceutical composition comprising: (a) an amount of a compound of the formula I, or a pharmaceutically acceptable salt thereof, that is effective in lowering the level of fructose in one or more of the tissues of a mammal, including a human, that are affected by diabetics; (b) an amount of an aldose reductase inhibiting compound, or a pharmaceutically acceptable salt thereof, that is effective in lowering the level of fructose in one or more of the tissues of a mammal, including a human, that are affected by diabetes and (c) a pharmaceutically acceptable carrier.

This invention also relates to a method of lowering the level of fructose in one or more of the tissues of a mammal, including a human, that are affected by diabetes, comprising administering to said mammal a fructose lowering effective amount of a compound of the formula I, or a pharmaceutically acceptable salt thereof, in combination with a fructose lowering effective amount of an aldose reductase inhibiting compound, or a pharmaceutically acceptable salt thereof.

This invention also relates to a pharmaceutical composition comprising: (a) an amount of a compound of the formula I, or a pharmaceutically acceptable salt thereof, effective in treating or preventing a diabetic complication such as diabetic neuropathy, diabetic retinopathy, diabetic nephropathy, or diabetic microangiopathy or macroangiopathy in a mammal, including a human; (b) an amount of an aldose reductase inhibiting compound, or a pharmaceutically acceptable salt thereof, effective in treating or preventing a diabetic complication such as diabetic neuropathy, diabetic retinopathy, diabetic nephropathy or diabetic microangiopathy or macroangiopathy in a mammal, including a human; and (c) a pharmaceutically acceptable carrier.

This invention also relates to a method of treating or preventing a diabetic complication such as diabetic neuropathy, diabetic retinopathy, diabetic nephropathy, or diabetic microangiopathy or macroangiopathy in a mammal, including a human, comprising administering to said mammal an amount of a compound of the formula I, or a pharmaceutically acceptable salt thereof, effective in treating or preventing such complication, in combination with an amount of an aldose reductase inhibiting compound, or a pharmaceutically acceptable salt thereof, effective in treating or preventing such complication.

This invention also relates to a pharmaceutical composition comprising: (a) an amount of a compound of the formula I, or a pharmaceutically acceptable salt thereof, that is effective in lowering the level of fructose in one or more of the tissues of a mammal, including a human, that are affected by diabetics; (b) an amount of a compound of the formula XV, XVI, XVII, XVIII or XIX, or a pharmaceutically acceptable salt thereof, that is effective in lowering the level of fructose in one or more of the tissues of a mammal, including a human, that are affected by diabetes and (c) a pharmaceutically acceptable carrier.

This invention also relates to a method of lowering the level of fructose in one or more of the tissues of a mammal, including a human, that are affected by diabetes, comprising administering to said mammal a fructose lowering effective amount of a compound of the formula I, or a pharmaceutically acceptable salt thereof, in combination with a fructose lowering effective amount of a compound of the formula XV, XVI, XVII, XVIII or XIX, or a pharmaceutically acceptable salt thereof.

This invention also relates to a pharmaceutical composition comprising: (a) an amount of a compound of the formula I, or a pharmaceutically acceptable salt thereof, effective in treating or preventing a diabetic complication such as diabetic neuropathy, diabetic retinopathy, diabetic nephropathy, or diabetic microangiopathy or macroangiopathy in a mammal, including a human; (b) an amount of a compound of the formula XV, XVI, XVII, XVIII or XIX, or a pharmaceutically acceptable salt thereof, effective in treating or preventing a diabetic complication such as diabetic neuropathy, diabetic retinopathy, diabetic nephropathy or diabetic microangiopathy or macroangiopathy in a mammal, including a human; and (c) a pharmaceutically acceptable carrier.

This invention also relates to a method of treating or preventing a diabetic complication such as diabetic neuropathy, diabetic retinopathy, diabetic nephropathy, or diabetic microangiopathy or macroangiopathy in a mammal, including a human, comprising administering to said mammal an amount of a compound of the formula I, or a pharmaceutically acceptable salt thereof, effective in treating or preventing such complication, in combination with an amount of a compound of the formula XV, XVI, XVII, XVIII or XIX, or a pharmaceutically acceptable salt thereof, effective in treating or preventing such complication.

Preferred embodiments of this invention include those pharmaceutical compositions and methods set forth above, wherein the compound of formula I, or pharmaceutically acceptable salt thereof, that is employed is a compound wherein $R^1$ is $(C_1-C_6)$hydroxyalkyl, $(C_1-C_6)$alkoxy, imidazolyl, furyl, pyrazolyl, tetrahydrofuryl, thienyl or triazolyl, or $R^1$ is Y—O—CH—$R^7$ wherein $R^7$ is benzothiazolyl, furyl, imidazolyl, pyrazolyl, thienyl, triazolyl, $(C_1-C_6)$alkyl or trifluoromethyl, and Y is hydrogen or $(C_1-C_6)$alkyl, and $R^2$ and $R^3$ form, together with the nitrogen to which they are attached, a group of the formula

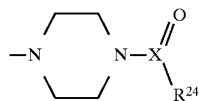

wherein X is carbon or —SO— and $R^{24}$ is amino, $(C_1-C_6)$alkylamino, di-$(C_1-C_6)$alkylamino or pyridyl.

Particularly preferred embodiments of this invention are those pharmaceutical compositions and methods referred to above, wherein the compound of formula I, or pharmaceutically acceptable salt thereof, that is employed is a compound wherein $R^1$ is $(C_1-C_6)$alkyl, $(C_1-C_6)$hydroxyalkyl, $(C_1-C_6)$alkoxy, furyl, triazolyl, or tetrahydrofuryl, or $R^1$ is

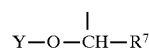

wherein $R^7$ is benzothiazolyl, furyl, thiazolyl, thienyl or trifluoromethyl, and Y is hydrogen or $(C_1-C_6)$alkyl, each of $R^4$ and $R^5$ is hydrogen, and $R^2$ and $R^3$, together with the nitrogen to which they are attached, form a group of the formula

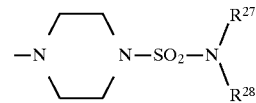

wherein $R^{27}$ and $R^{28}$ are, independently, methyl or ethyl.

Other particularly preferred embodiments of this invention are those pharmaceutical compositions and methods referred to above, wherein the compound of formula I, or pharmaceutically acceptable salt thereof, that is employed is a compound wherein $R^1$ is $(C_1-C_6)$hydroxyalkyl, furyl or triazolyl, or $R^1$ is

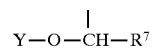

wherein $R^7$ is furyl, thienyl or trifluoromethyl and Y is hydrogen, each of $R^4$ and $R^5$ is hydrogen, and $R^2$ and $R^3$, together with the nitrogen to which they are attached, form a group of the formula

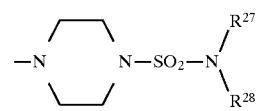

wherein $R^{27}$ and $R^{28}$ are, independently, hydrogen, methyl or ethyl.

Preferred embodiments of this invention also include the pharmaceutical compositions and methods set forth above, wherein the compound of formula I, or pharmaceutically acceptable salt thereof, that is employed is selected from:

4-[4-(N-methylsulfamoyl)-piperazino]-2-methylpyrimidine;

4-[4-(N-sulfamoyl)-piperazino]-2-methylpyrimidine;

4-[4-(N,N-dimethylsulfamoyl)-piperazino]-2-methylpyrimidine;

4-[4-(N-methylsulfamoyl)-piperizino]-2-hydroxymethylpyrimidine;

4-[4-(N-sulfamoyl)-piperizino]-2-hydroxymethylpyrimidine; and

4-[4-(N,N-dimethylsulfamoyl)-piperizino]-2-hydroxymethylpyrimidine.

Preferred embodiments of this invention also include those pharmaceutical compositions and methods set forth above that comprise or employ a composition comprising an aldose reductase inhibitor selected from:

(4-amino-2,6-dimethylphylsulfonyl)nitromethane;

N,N-diisopropyl-N'-[3,5-dimethyl-4-(nitromethylsulfonyl)phenyl]oxamide;

N-[3,5-dimethyl-4-(nitromethylsulfonyl)phenyl]-2-(piperidino)glyoxamide;

[2,6-dimethyl-4-(phenylacetamido)phenylsulfonyl]nitromethane;

[2,6-dimethyl-4-(2-phenoxyacetamido)phenylsulfonyl]nitromethane;

[2,6-dimethyl-4-(2-(3-methylphenoxyacetamido)phenyl)sulfonyl]nitromethane;

[2,6-dimethyl-4-(2-(3-chlorophenoxyacetamido)phenyl)sulfonyl]nitromethane;

[2,6-dimethyl-1-((2,4,6-trimethylphenyl)acetamido)
  phenylsulfonyl]nitromethane;
2,6-dimethyl-4-((2-methylphenyl)acetamido)
  phenylsulfonyl nitromethane;
2,6-dimethyl-4-((2-fluorophenyl)acetamido)
  phenylsulfonyl nitromethane;
2-(nitromethylsulfonyl)thiophene;
2-chloro-5-(nitromethylsulfonyl)thiophene;
N-(nitromethylsulfonyl)morpholine;
N-(nitromethylsulfonyl)piperidine;
N-(nitromethylsulfonyl)indoline;
d-6-fluoro-spiro(chroman-4,4'-imidazolidine)-2',5'-dione;
2-fluoro-spiro(9H-fluorene-9,4'-imidazolidine)-2',5'-
  dione;
2,7-difluoro-spiro(9H-fluorene-9,4'-imidazolidine)-2',5'-
  dione;
2,7'-difluoro-5-methoxy-spiro(9H-fluorene-9,4'-
  imidazolidine)-2',5'-dione;
7-fluoro-spiro(5H-indenol[1,2-b]pyridine-5,3'-
  pyrrolidine)2,5'-dione;
d-cis-6'-chloro-2',3'-dihydro-2'-methyl-spiro-
  (imidazolidine-4,4'-4'H-pyrano(2,3-b)pyridine)-2,5-
  dione;
Spiro [imidazolidine4,5'(6H)-quinoline]2,5-dione-3'-
  chloro-7',8'-dihydro-7'-methyl-, (5'S-cis); and
(2S,4S)-6-fluoro-2',5'-dioxospiro(chroman-4,4'-
  imidazolidine)-2-carboxamide.

"A sorbitol dehydrogenase inhibiting effective amount of a compound of the formula I, or a pharmaceutically acceptable salt thereof," as used herein, refers to an amount of a compound of the formula I, or a pharmaceutically acceptable salt thereof, that exhibits sorbitol dehydrogenase inhibiting activity, or an amount of such compound or salt that yields a metabolite in vivo that exhibits sorbitol dehydrogenase inhibiting activity.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

The acids that may be used to prepare pharmaceutically acceptable acid addition salts of those compounds of formulae I and VI that are basic in nature are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzene-sulfonate, p-toluenesulfonate and pamoate [i.e., 1,1'-methylene-bis-(2-hydroxy-3-naphthoate)] salts. The chemical bases that may be used as reagents to prepare pharmaceutically acceptable base salts of those compounds of formulae I and VI that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

DETAILED DESCRIPTION OF THE INVENTION

Many of the substituted pyrimidines of the formula I are known compounds. These may be prepared from commercially available or known starting materials by the procedures set forth in European Patent Application 470616A2, published Feb. 12, 1992 and European Patent Application 384,370A1, published Aug. 29, 1990.

Compounds of the formula XV may be prepared as described in U.S. Pat. No. 4,130,714, which issued to Reinhard Sarges on Dec. 19, 1978, U.S. Pat. No. 5,066,659 which issued to Christopher A. Lipinski on Nov. 19,1991, U.S. Pat. No. 4,566,670, which issued to Christopher A. Lipinski on Dec. 3, 1985, U.S. Pat. No. 4,980,357, which issued to Goldstein et al. on Dec. 25, 1990, U.S. Pat. No. 4,540,704, which issued to Ueda et al. on Sep. 10, 1985, and U.S. Pat. No. 4,985,573, which issued to Kurono et al. on Jan. 15, 1991. Compounds of the formula XVI may be prepared as described in U.S. Pat. Nos. 4,436,745 and 4,438,272, which issued to Billie M. York, Jr. on Mar. 13, 1984 and Mar. 20, 1984, respectively. All of the foregoing documents are incorporated herein by reference in their entirety.

Compounds of the formulae VII and VIII may be prepared as described in U.S. Pat. No. 5,039,672, which issued to Eggler et al. on Aug. 13,1991. Compounds of the formula XIX may be prepared as described in European Patent Applications EP 304190, EP 408713, EP 409449, EP 469887 and EP 469888, which were published, respectively, on Feb. 22, 1989, Jan. 23, 1991, Jan. 30, 1991, Feb. 5, 1992 and Feb. 5, 1992, U.S. Pat. No. 5,110,808, which issued to Briftain et al. on May 5, 1992, U.S. Pat. No. 5,102,905, which issued to Brown et al. on Apr. 7, 1992, and U.S. Pat. No. 5,096,918, which issued to Keith B. Mallion on Mar. 17, 1992. All of the foregoing documents are incorporated herein by reference in their entirety.

Compounds of the formula

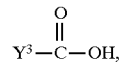

wherein $Y^3$ is a group of the formula VII, as defined above, may be prepared as described in U.S. Pat. No. 4,251,528, which issued to Brittain et al. on Feb. 17, 1981, U.S. Pat. No. 4,996,204, which issued to Mylari et al. on Feb. 26, 1991, U.S. Pat. No. 4,939,140, which issued to Larsen et al. on Jul. 3, 1990, PCT Patent Application PCT/US 92/01603, which was filed on Mar. 9, 1992, European Patent Application EP 436307, which was published on Jul. 10, 1991, and French Patent Application FR 2647676A1, which was published on Dec. 7, 1990. Compounds of the formula

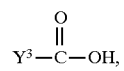

wherein $Y^3$ is a group of the formula IX, as defined above, may be prepared as described in U.S. Pat. No. 4,464,382, U.S. Pat. No. 4,791,126 and U.S. Pat. No. 4,831,045, which issued to Tanouchi et al. on, respectively, Aug. 7, 1984, Dec. 13, 1988 and May 16, 1989. All of the foregoing documents are incorporated herein by reference in their entirety.

Compounds of the formula

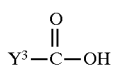

wherein $Y^3$ is a group of the formula X, as defined above, may be prepared as described in U.S. Pat. No. 4,391,825, which issued to Bellini et al. on Jul. 5, 1983, and in U.S. Pat. No. 4,568,693, U.S. Pat. No. 4,600,724 and U.S. Pat. No. 4,705,882, which issued to Sestanj et al. on, respectively, Feb. 4, 1986, Jul. 15, 1986 and Nov. 10, 1987. Compounds of the formula

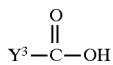

wherein $Y^3$ is a group of the formula XI, as defined above, may be prepared as described in U.S. Pat. No. 4,771,050, which issued to Meguro et al. on Sep. 13, 1988. Compounds of the formula

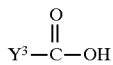

wherein $Y^3$ is a group of the formula XII, as defined above, may be prepared as described by Billon et al., *Eur. J. Med. Chem.*, 25, 121 (1990). All of the foregoing documents are incorporated herein by reference in their entirety.

Compounds of the formula

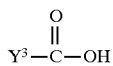

wherein $Y^3$ is a group of the formula XIII, as defined above, may be prepared as described in U.S. Pat. No. 4,883,410, which issued to Christopher A. Lipinski on Aug. 1, 1989. Compounds of the formula

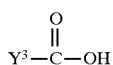

wherein $Y^3$ is a group of the formula XIV, as defined above, may be prepared as described in European Patent Application 325375, which was published on Jul. 26, 1989. Compounds of the formula

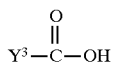

wherein $Y^3$ is a group of the formula XIVA, as defined above, may be prepared as described in European Patent Application 492667A1, which was published on Jul. 1, 1992. All of the foregoing documents are incorporated herein by reference in their entirety.

Methods of preparing the various compounds and compositions of this invention are described below. Unless otherwise noted, in the reaction schemes and discussion that follow, $R^1$ through $R^{28}$, Q, W, Y, $Y^2$, $Y^3$, $Y^4$ $Y^5$, A, B, D, E, G, J, L, and M are defined as above.

Reaction schemes 1–3 below illustrate methods of preparing the novel compounds of the formula IA.

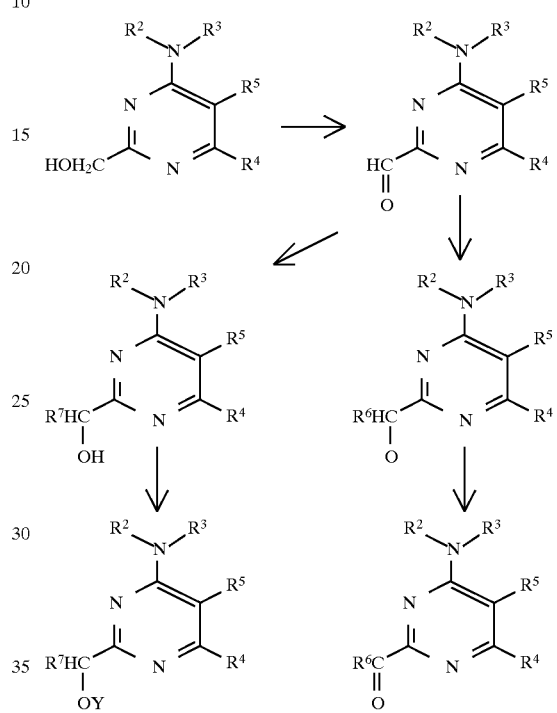

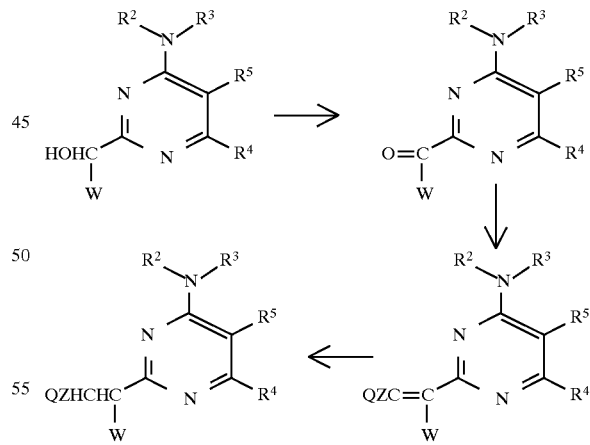

SCHEME 3

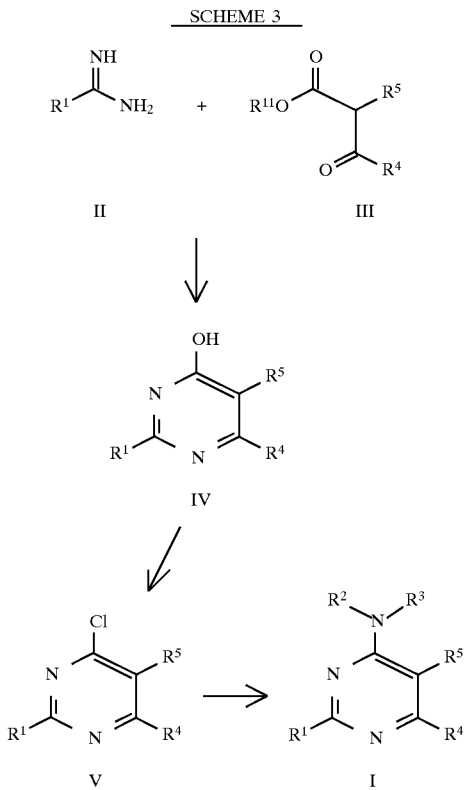

(R¹ = optionally substituted aryl,
optionally substituted heteroaryl,
dihydroxy-($C_1$–$C_6$)alkyl,
($C_1$–$C_6$)alkyl-S-($C_1$–$C_6$)alkyl,
aryl-($C_1$–$C_6$)alkyloxy wherein the
aryl moiety is optionally substituted,
aryl-($C_1$–$C_6$)alkyl wherein the aryl
moiety is optionally substituted,
or heteroaryl-($C_1$–$C_6$)alkyl wherein
the heteroaryl moiety is optionally
substituted)

Referring to scheme 1, compounds of the formula IA wherein R¹ is

and $R^6$ is hydrogen may be prepared by oxidizing the corresponding compounds wherein $R^1$ is hydroxymethyl (—$CH_2OH$). Oxidizing agents that may be used include chromic acid, silver oxide and activated manganese dioxide, with activated manganese dioxide being preferred. When chromic acid is used, the preferred solvent is water or an aqueous ($C_3$–$C_6$)alkyl ketone (e.g., acetone) and the reaction temperature, which can range from about –78° C. to about 250° C., is preferably from about –10 °C. to about 0° C. When silver oxide or activated manganese dioxide is used, the solvent is preferably a halocarbon solvent such as chloroform or methylene chloride, and the reaction temperature, which can range from about 0° C. to about 100° C., is preferably between about 20° C. and the reflux temperature of the solvent.

Compounds of the formula IA wherein $R^1$ is

and $R^6$ is other than hydrogen may be prepared by first reacting the corresponding compound wherein $R^1$ is formyl (CHO) with an organolithium reagent of the formula $R^6Li$ or an appropriate Grignard reagent of the formula $R^6MgX$ wherein X is chloro, bromo or iodo, and then oxidizing the reaction product. The initial reaction with the Grignard or organolithium reagent is generally conducted in a hydrocarbon solvent such as n-pentane, n-hexane or n-heptane, at a temperature from about –70° C. to about 0° C., preferably from about –70° C. to about –20° C. The subsequent oxidation step may be carried out as described above for the oxidation of compounds wherein $R^1$ is hydroxymethyl.

Compounds of the formula IA wherein $R^1$ is $$\underset{}{YOCHR^7}$$

and Y is hydrogen may be prepared by reacting the corresponding compounds wherein $R^1$ is

with an organolithium reagent of the formula $R^7Li$ or an appropriate Grignard reagent of the formula $R^7MgX$, in the manner described above for preparing compounds of the formula I wherein $R^7$ is $$\overset{O}{\underset{}{\|}}-CR^6$$

and $R^6$ is other than hydrogen. Treatment of the resulting compounds with an appropriate reagent of the formula Y—L, wherein Y is other than hydrogen and L is a leaving group, in the presence of a strong base yields the corresponding compounds wherein $R^1$ is

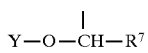

and Y is other than hydrogen. Examples of bases that may be used are sodium hydride in dimethylformamide and a ($C_1$–$C_6$)alkyllithium in a hydrocarbon solvent (e.g. n-pentane or n-hexane). Suitable leaving groups include chloro, bromo, iodo and $OSO_2$—($C_1$–$C_6$)-alkyl. The reaction temperature can range from about –20° C. to about 100° C., and is preferably from about 0° C. to about 60° C.

Scheme 2 illustrates the preparation of compounds of the formula IA wherein $R^1$ is a group of the formula

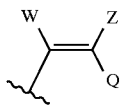

Referring to scheme 2, such compounds may be prepared by reacting the corresponding compounds wherein $R^1$ is

with a Wittig reagent of the formula

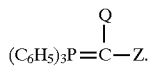

Typically, this reaction is carried out in a nonprotic solvent such as dimethylformamide or a ($C_4$–$C_6$)alkylether, preferably tetrahydrofuran, at a temperature from about 0° C. to about 100° C., preferably from about 25° C. to about 100° C. The reactants in which $R^1$ is

may be obtained by oxidation of the corresponding compounds wherein $R^1$ is —CHOHW as described above for the oxidation of compounds wherein $R^1$ is —CHOHR$^6$. Similarly, those compounds wherein $R^1$ is —CHOHW may be obtained by the procedure described above and depicted in scheme 1 for preparing the analogous compounds wherein $R^1$ is —CHOHR$^6$ or —CHOHR$^7$.

Compounds of the formula IA wherein $R^1$ is a group of the formula

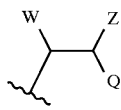

may be formed by hydrogenation of the corresponding compounds wherein $R^1$ is

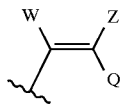

in the presence of a metal containing catalyst. Suitable hydrogenation catalysts include palladium, platinum, nickel, platinum oxide and rhodium. The preferred catalyst for hydrogenation is platinum on carbon. The reaction temperature may range from about 10° C. to about 50° C., with about 25° C. being preferred. The hydrogenation is generally carried out at a pressure from about 1.5 to about 4 atmospheres, preferably at about 3.0 atmospheres, in a suitable inert solvent such as acetic acid or a lower alcohol, preferably methanol, with about a stoichiometric quantity of hydrogen chloride present.

Compounds of the formula IA wherein $R^1$ is optionally substituted aryl, optionally substituted heteroaryl, dihydroxy-($C_1$–$C_6$)alkyl or ($C_1$–$C_6$)alkyl-S—($C_1$–$C_6$)alkyl may be prepared according to the reaction sequence illustrated and scheme 3. This reaction sequence is the same as that described in European Patent Applications 470616A2 and 384370A1, referred to above, with the exception that a compound of the formula $R^1C$=$NHNH_2$, wherein $R^1$ is defined as above, is used as a starting material. The conditions, reagents and catalysts, etc. used in the reactions of scheme 3 are set forth in detail in the foregoing patent applications, which, as indicated above, have been incorporated herein by reference in their entirety.

Referring to scheme 3, a compound of formula II or its acid addition salt is reacted with a compound of formula III to give a compound of formula IV. The reaction is generally conducted or an alcoholic solvent such as methanol, ethanol or tert-butanol, at a temperature from about 25° C. to about 100° C., preferably from about 25° C. to about 50° C. When an acid addition salt of a compound of formula II is employed, the reaction is generally conducted as above in the presence of an alkali metal or alkaline earth metal hydroxide (e.g., sodium, potassium, or calcium hydroxide) or an alkali metal alkoxide (e.g., sodium or potassium ethoxide or tert-butoxide) at temperatures ranging from about 10° C. to about 80° C., preferably at temperatures between 30° and 60° C.

The compound of formula IV is converted into a pyrimidine derivative of the formula V by reacting it with an inorganic acid chloride, e.g., phosphorus oxychloride, thienyl chloride, phosphorus pentachloride or phosphorous trichloride. This reaction is usually conducted in an aromatic hydrocarbon solvent, e.g., benzene, toluene or xylene, at a temperature from about 30° to about 100° C. The preferred temperature range is between 30° and 60° C.

Reaction of the compound of formula V with the appropriate compound of formula $NHR^2R^3$ yields a compound of formula IA. Suitable solvents for this reaction include ethereal solvents such as ethyl ether, tetrahydrofuran, or dioxane and halocarbon solvents such as methylene chloride or chloroform. The reaction temperature may range from about 0° C. to about 80° C. Preferably, the solvent is a halocarbon solvent and the temperature is between 0° C. and 50° C.

Compounds of the formula IA wherein $R^1$ is ($C_1$–$C_6$) alkoxycarbonyl-($C_1$–$C_6$)alkyl may be prepared by reacting the corresponding compounds wherein $R^1$ is hydroxy-($C_1$–$C_6$)alkyl with the appropriate ($C_1$–$C_5$)alkanoic acid chloride in the presence of an organic base. Examples of suitable organic bases are ($C_4$–$C_{10}$)alkylamines and dialkylamines, pyridine, quinoline and isoquinoline. Generally, this reaction is carried out in another or halocarbon solvent such as diethyl ether, tetrahydrofuran (THF), methylene chloride or chloroform, at a temperature from about 0° C. to about 50° C., preferably from about 0° C. to about room temperature.

Compounds of the formula IA wherein $R^1$ is ($C_1$–$C_6$) alkoxycarbonylaryl can be prepared in a similar manner, using the appropriate aroyl chloride in place of a ($C_1$–$C_5$) alkanoic acid chloride.

Compounds of the formula IA wherein $R^1$ is ($C_1$–$C_6$) alkyl-SO—($C_1$–$C_6$)alkyl may be prepared by oxidation of the corresponding compounds wherein $R^1$ is ($C_1$–$C_6$)alkyl-S—($C_1$–$C_6$)alkyl using methods well known to those skilled in the art. For example, these oxidations may be conducted using m-chloroperbenzoic acid as the oxidizing agent in a halocarbon solvent such as methylene chloride or chloroform, at a temperature from about −10° C. to about 10° C., preferably about 0° C. Similarly, compounds of the formula IA wherein $R^1$ is ($C_1$–$C_6$)alkyl-$SO_2$—($C_1$–$C_6$)alkyl may be prepared by oxidation of the corresponding compounds wherein $R^1$ is ($C_1$–$C_6$)alkyl-SO—($C_1$–$C_6$)alkyl using methods known in the art. Such oxidations may be conducted, for example, in the manner specified above, but at a temperature ranging from about room temperature to about 60° C., preferably at about the reflux temperature of the solvent.

Compounds of the formula VI can be prepared using methods that are well known in peptide chemistry. Some of these procedures are described below.

Compounds of the formula VI wherein $R^{25}$ $$Y^3-\overset{O}{\underset{\|}{C}}-O-Y^2-$$

and $Y^2$ is absent can be prepared as follows. A compound of the formula $$Y^3-\overset{O}{\underset{\|}{C}}-OH$$

is first converted into its corresponding acid chloride, $$Y^3-\overset{O}{\underset{\|}{C}}-Cl,$$

by reacting it with thionyl chloride in a suitable aromatic or halocarbon solvent (e.g., benzene, toluene, xylene, methylene chloride or chloroform), at a temperature from about 0° C. to about 130° C., preferably from about 20° C. to about 100° C. The acid chloride is then reacted with a compound having the following formula

XX to produce the corresponding compound of formula VI wherein $Y^2$ is absent. This reaction is generally carried out in a halocarbon, aromatic hydrocarbon or ethereal solvent at a temperature from about 0° C. to about 150° C., preferably from about 0° C. and about 100° C. Preferred solvents include benzene, toluene, xylene, methylene chloride, chloroform, ether, tetrahydrofuran and dioxane.

Alternatively, compounds of the formula VI wherein $Y^2$ is absent can be prepared by reacting a compound of the formula $$Y^3-\overset{O}{\underset{\|}{C}}-OH$$

with a $(C_4-C_8)$alkylchloroformate in the presence of any organic base, and then adding a compound of the formula XX, as depicted and defined above, to the reaction mixture. Examples of bases that may be used are $(C_3-C_6)$alkylamines and aromatic amines such as pyridine, quinoline or isoquinoline. This reaction is typically conducted in a halocarbon solvent, preferably methylene chloride or chloroform, at a temperature from about −70° C. to about 50° C., preferably from about −70° C. to about 20° C.

The addition of the compound of formula XX is typically carried out at temperatures ranging from about −70° C. to about 50° C., preferably from about −70° C. and about 30° C.

Compounds for the formula VI wherein $R^{25}$ is $$Y^3-\overset{O}{\underset{\|}{C}}-O-Y^2-$$

and $Y^2$ is $$-\overset{O}{\underset{\|}{C}}-O-$$

can be prepared by the following procedure. A compound of the formula XX, as depicted and defined above, is reacted with phosgene, to obtain a compound of the formula

XXI

This reaction is conducted in the presence of a base (e.g., a $(C_3-C_{10})$alkylamine or an aromatic amine such as pyridine, quinoline or isoquinoline) at a temperature from about −70° C. to about 0° C., preferably from about −30° C. to about 0° C. Appropriate solvents include ethereal, halocarbon and $(C_5-C_{10})$hydrocarbon solvents. Ether, dioxane, tetrahydrofuran, pentane, hexane, methylene chloride and chloroform are preferred. The compound of formula XXI formed in the above reaction is then reacted with a compound of the formula $$Y^3-\overset{O}{\underset{\|}{C}}-OH$$

in the presence of abase (e.g., a $(C_3-C_{10})$alkylamine or an aromatic amine such as pyridine, quinoline or isoquinoline). The reaction is generally conducted at a temperature ranging from about −20° C. to about room temperature, preferably between about −10° C. and about room temperature, in a halocarbon or ether solvent, preferably in methylene chloride or chloroform.

Compounds of the formula VI wherein $R^{25}$ is $$Y^3-\overset{O}{\underset{\|}{C}}-O-Y^2-$$

and $Y^2$ is $$-CH_2-\overset{Y^4}{\underset{|}{}}\overset{O}{\underset{\|}{C}}-O-$$

may be prepared in the following manner. First, a compound of the formula $$Y^3-\overset{O}{\underset{\|}{C}}-OH$$

is contacted with an Ameberlite® IRA-904 resin containing quaternary ammonium groups in the hydroxide form to yield a salt of the formula $$Y^3-\overset{O}{\underset{\|}{C}}-O^-\overset{Resin}{\underset{|}{N(CH_3)_3}}$$

(hereinafter referred to as a salt of the formula XXII). Usually, the compound of formula

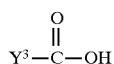

is dissolved in a lower alcohol or hydrocarbon solvent such as ethanol, diethyl ether or hexane and the reaction is carried out at a temperature from about 10° C. to about 50° C., preferably at about room temperature. Then, a compound having a formula identical to formula VI except that $R^{25}$ is replaced by a hydroxy group is reacted with a compound of the formula

wherein $Y^4$ is hydrogen or $(C_1-C_5)$alkyl, in the presence of an organic base. Bases that may be used include $(C_4-C_{10})$ alkylamines and dialkylamines, pyridine, quinoline and isoquinoline. Suitable solvents include ether and hydrocarbon solvents such as diethyl ether, methylene chloride, tetrahydrofuran and chloroform. Reaction temperatures may range from about 0° C. to about 50° C., and are preferably between about 0° C. and about room temperature.

The foregoing reaction produces a compound of the formula VI wherein $R^{25}$ is

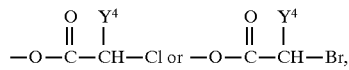

which is then reacted with the salt of formula XXII to produce the desired compound of formula VI. This reaction is generally conducted in an ether, halocarbon or hydrocarbon solvent (e.g., diethyl ether, hexane, methylene chloride or chloroform) at a temperature from about room temperature to about 60° C., preferably at about room temperature.

Compounds of the formula VI wherein $R^{25}$ is

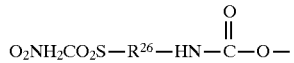

may be prepared by reacting a compound of the formula

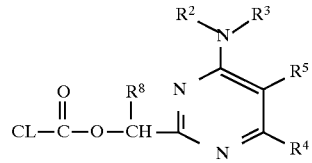

with a compound of the formula $O_2NCH_2SO_2-R^{26}-NH_2$.

Typically, this reaction is carried out in an ethereal, halocarbon or hydrocarbon solvent at temperatures from about –70° C. to about 0 °C. Preferably, it is carried out in ether, tetrahydrofuran, dioxane, hexane, pentane, methylene chloride or chloroform at a temperature from about –30° C. to about 0° C.

Alternatively, such compounds can be prepared by reacting an isocyanate of the formula

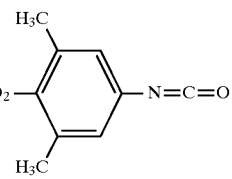

with a compound of the formula XX, as depicted and defined above. Suitable and preferred solvents for this reaction are similar to those specified for the preceding reaction. This reaction is usually conducted at a temperature ranging from about ambient temperature to about 150° C., preferably from about ambient temperature to about 100° C.

The starting material of the formula XXIII can be prepared from the compound

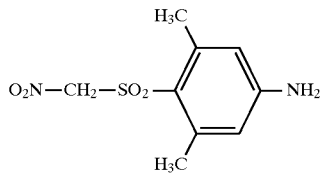

using standard methods described in the scientific literature.

In each of the reactions discussed or illustrated above, pressure is not critical unless otherwise indicated. Pressures from about 0.5 atmospheres to about 5.0 atmospheres are generally acceptable, and ambient pressure, i.e., about one atmosphere, is preferred as a matter of convenience. Reaction times also are not critical unless otherwise indicated. Reaction times from about 0.5 hours to about 3 hours are generally acceptable, though longer reaction times (e.g., 24 or 48 hours) may be employed as a matter of convenience. Reaction times are monitored by thin layer chromatography.

The pharmaceutically acceptable acid addition salts of the compounds of the formulae I and VI that are basic in nature may be prepared in a conventional manner by treating a solution or suspension of the free base of formula I or VI with about one chemical equivalent of a pharmaceutically acceptable acid. Conventional concentration and recrystallization techniques are employed in isolating the salts.

The pharmaceutically acceptable base addition salts of compounds of the formulae I and VI that are acidic in nature may be formed with pharmaceutically acceptable cations by conventional methods. Thus, these salts may be readily prepared by treating the compound of formula I or VI with an aqueous solution of the desired pharmaceutically acceptable cation and evaporating the resulting solution to dryness, preferably under reduced pressure. Alternatively, a lower alkyl alcohol solution of the compound of formula I or VI may be mixed with an alkoxide of the desired metal and the solution subsequently evaporated to dryness.

Compounds of the formula I, the pharmaceutically acceptable salts of such compounds, mutual prodrugs of such compounds and aldose reductase inhibitors (including the mutual prodrugs of the formula VI), the pharmaceutically acceptable salts of such mutual prodrugs, and compositions comprising a compound of the formula I or a pharmaceutically acceptable salt thereof and an aldose reductase inhibitor or a pharmaceutically acceptable salt thereof (including compositions containing a compound of the formula I and a compound of the formula XV, XVI, XVII, XVIII or XIX) are hereinafter referred to, collectively, as "the active compounds and compositions of this invention".

The active compounds and compositions of this invention may be administered to a subject in need of treatment by a variety of conventional routes of administration, including orally, parenterally and topically. In general, compounds of the formula I and their pharmaceutically acceptable salts will be administered orally or parenterally at dosages between about 0.1 and about 50 mg/kg body weight of the subject to be treated per day, preferably from about 0.1 to 15 mg/kg, in single or divided doses. Mutual prodrugs of compounds of the formula I and aldose reductase inhibitors will generally be administered orally or parenterally at dosages between about 5 and about 100 mg/kg body weight of the subject to be treated per day, preferably from about 5 to about 25 mg/kg, in single or divided doses. Compositions containing both a compound of the formula I and an aldose reductase inhibitor will generally be administered orally or parenterally at dosages between about 1 and about 100 mg of each active component (i.e., the compound of formula I and the aldose reductase inhibitor) per kg body weight of the subject to be treated per day, preferably from about 1 to about 25 mg/kg. However, some variation in dosage will necessarily occur depending on the condition of the subject being treated. The person responsible for administration will, in any event, determine the appropriate dose for the individual subject.

The active compounds and compositions of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of this invention and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compounds and compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are, especially suitable for intravenous, intramuscular, subcutaneous and intraperitoneal administration. In this connection, the sterile aqueous media employed are all readily available by standard techniques known to those skilled in the art.

The active compounds and compositions of this invention may be more particularly employed in the preparation of ophthalmic solutions. Such ophthalmic solutions are of principal interest for the treatment of diabetic cataracts by topical administration. For the treatment of diabetic cataracts, the active compounds and compositions of this invention are administered to the eye in the form of an ophthalmic preparation prepared in accordance with conventional pharmaceutical practice. The ophthalmic preparation will contain a compound of the formula I, a mutual prodrug of a compound of the formula I and an aldose reductase inhibitor, or a pharmaceutically acceptable salt of such compound of formula I or prodrug, in a concentration from about 0.01 to about 1% by weight, preferably from about 0.05 to about 0.5%, in a pharmaceutically acceptable solution, suspension or ointment. In opthalmic preparations containing a combination of a compound of the formula I and an aldose reductase inhibitor, each active ingredient will be present in an amount from about 0.005 to about 1% by weight, preferably from about 0.005 to about 0.25%, in a pharmaceutically acceptable solution, suspension or ointment.

EXAMPLES

General Experimental Procedure

Male Sprague-Dawley rats (350–400 g) were used for these experiments. Diabetes was induced in some of the rats by a tail vein injection of streptozocin, 85 mg/kg. Twenty-four hours later, 4 groups of diabetic rats were given a single dose of 4-[4-(N,N-dimethylsulfamoyl)-piperazino]-2-methylpyrimidine(10, 50, 100, or 300 mg/kg) by oral gavage. Animals were sacrificed 4–6 hours after dosing and blood and sciatic nerves were harvested. Tissues and cells were extracted with 6% perchloric acid.

Sorbitol in erythrocytes and nerves was measured by a modification of the method of R. S. Clements et al. (Science, 166: 1007–8, 1969). Aliquots of tissue extracts were added to an assay system which had final concentrations of reagents of 0.033M glycine, pH 9.4, 800 $\mu$M β-nicotine adenine dinucleotide, and 4 units/ml of sorbitol dehydrogenase. After incubation for 30 minutes at room temperature, sample fluorescence was determined on a fluorescence spectrophotometer with excitation at 366 nm and emission at 452 nm. After subtracting appropriate blanks, the amount of sorbitol in each sample was determined from a linear regression of sorbitol standards processed in the same manner as the tissue extracts.

Fructose was determined by a modification of the method described by M. Ameyama, *Methods in Enzymology*, 89: 20–25 (1982). Resazurin was substituted for ferricyanide. Aliquots of tissue extracts were added to the assay system, which had final concentrations of reagents of 1.2M citric acid, pH 4.5, 13 $\mu$M resazurin, 3.3 units/ml of fructose dehydrogenase and 0.068% Triton X-100. After incubation for 60 minutes at room temperature, sample fluorescence was determined on a fluorescence spectrophotometer with excitation at 560 nm and emission at 580 nm. After subtracting appropriate blanks, the amount of fructose in each sample was determined from a linear regression of fructose standards processed in the same manner as the tissue extracts.

SDH activity was measured by a modification of the method described by U. Gerlach, *Methodology of Enzymatic Analyses*, edited by H. U. Bergmeyer, 3, 112–117 (1983). Aliquots of sera or urine were added to the assay system, which had final concentrations of reagents of 0.1M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance was determined at 340 nm. SDH activity was presented as milliOD$_{340}$ units/minute (OD$_{340}$=optical density at 340 nm).

Results

As shown in FIG. 1, 4-[4-(N,N-dimethylsulfamoyl)-piperazino]-2-methyl-pyrimidine ("Compound 1") dose dependently lowered erythrocyte (red blood cell—"RBC") fructose in diabetic rats. It dose dependently raised erythrocyte sorbitol in diabetic rats (FIG. 2). A similar lowering of fructose with an increase in sorbitol was seen in the sciatic nerve of diabetic rats (FIGS. 3 and 4).

This pattern of lowered fructose coupled with elevated sorbitol is consistent with that expected of an inhibitor of sorbitol dehydrogenase (SDH), the enzyme that converts sorbitol to fructose. However, when tested directly on sorbitol dehydrogenase in vitro, 4-[4-(N,N-dimethylsulfamoyl)-piperazino]-2-methylpyrimidine exhibited an IC$_{50}$ value of 0.5 mM. On the other hand, we discovered that sera from rats dosed with 4-[4-(N,N-dimethylsulfamoyl)-piperazino]-2-methylpyrimidine potently inhibited SDH in vitro in a dose dependent manner (FIG. 5).

The urine of animals dosed with 4-[4-(N,N-dimethylsulfamoyl)-piperazino]-2-methylpyrimidine also potently inhibited SDH in vitro in a dose dependent manner (FIG. 6). Comparison with results for the sera (FIG. 5) shows that the urine was an even more potent source of SDH inhibitory activity, with strong inhibition of SDH found with as little as 0.5 μl of urine.

Examples 1, 2 and 3

Example 1

4-[4-(N-methylsulfamoyl)-piperazino]-2-methylpyrimidine

Example 2

4-[4-N-methylsulfamoyl)-piperazino]-2-hydroxymethylpyrimidine

Example 3

4-[4-N-sulfamoyl)-piperazino]-2-methylpyrimidine

An aqueous suspension of 4-[4-(N,N-dimethylsulfamoyl)-piperazino]-2-methylpyrimidine ("Compound 1"), prepared as described in European Patent Application 384,370A1, was administered by oral gavage to male CD rats (350–430 g body weight) at a dose of 100 mg/kg. The rats were housed in appropriate cages and their urine (220 mL) was collected overnight. The urine was extracted with ethyl acetate (75 mL) and the resulting emulsion was filtered through a supercel pad and the filtrate was collected. The ethyl acetate layer was separated and the aqueous layer was extracted again (3×75 mL). The ethyl acetate extracts were combined and dried over anhydrous magnesium sulfate to obtain a crude oily residue (0.8 g). This residue was dissolved in 10 mL of a 9:1 mixture of methylene chloride and ethanol and chromatographed using a Chromatotron. The Chromatotron plate was eluted with a mixture of 19:1 of methylene chloride and ethanol and fractions were collected in 5 mL portions. Evaporation of the first 20×5 mL portions gave the title compound of Example 1 (6.9 mg): $^1$H NMR (DMSO, 500 MHz) δ 2.37 (s, 3H), 2.55 (d, J=7 Hz, 3H), 3.13 (m, 4H), 3.7 (m, 4H), 6.68 (d, J=8 Hz, 1H), 7.72 (m, 1H), 8.13 (d, J=8 Hz, 1H). The next 20×5 mL portions yielded the title compound of Example 2 (24 mg): $^1$H NMR (DMSO, 500 MHz) δ 2.48 (d, J=7 Hz, 3H), 3.1 (m, 4H), 3.58 (m, 4H), 4.36 (s, 2H), 6.1 (s, 1H), 6.33 (d, J=8 Hz, 1H), 6.5 (m, 1H), 8.03 (d, J=8 Hz, 1H). The last 20×5 mL portions gave the title compounds of Example 3 (15 mg): $^1$H NMR (DMSO, 500 MHz) δ 2.34 (s, 3H), 3.04 (m, 4H), 3.65 (m, 4H), 6.35 (d, J=8 Hz, 1H), 7.93 (d, J=8 Hz, 1H).

Example 4

4[4-(N,N-Dimethylsulfamoyl)piperizino]-2-hydroxymethylpyrimidine

The title compound was prepared as described in European Patent Application 470,616A2, published Feb. 12, 1992.

The structures and IC$_{50}$ values of 4-[4-(N,N-dimethylsulfamoyl)-piperazino]-2-methylpyrimidine and the title compounds of Example 1–4 are set forth in Table I below. The IC$_{50}$ values indicate the concentration at which fifty percent inhibition of sorbitol dehydrogenase in vitro was observed.

TABLE 1

| 4-[4-(N,N-dimethylsulfamoyl)-piperazino]-2-methylpyrimidine (Compound 1) | (Example 1) | (Example 2) | (Example 3) | (Example 4) |
| --- | --- | --- | --- | --- |
| SO$_2$N(CH$_3$)$_2$ / piperazine / 2-methylpyrimidine | SO$_2$NCH$_3$ / piperazine / 2-methylpyrimidine | SO$_2$NHCH$_3$ / piperazine / 2-CH$_2$OH-pyrimidine | SO$_2$NH$_2$ / piperazine / 2-methylpyrimidine | SO$_2$N(CH$_3$)$_2$ / piperazine / 2-CH$_2$OH-pyrimidine |
| IC$_{50}$ (μM) 480 | 5 | 1 | 12 | 0.14 |

Example 5

4[4-(N,N-Dimethylsulfamoyl)piperizino]pyrimidine-2-ylmethyl-3,4-dihydro-4-oxo-3-[[(5-trifluoromethyl)-2-benzothiazolyl]-methyl]-1-phthalazine acetate A solution of 3,4-dihydro-4-oxo-3-[[(5-trifluoromethyl)-2-benzothiazolyl]-methyl]-1-phthalazineacetic acid (839 mg, 2 mmol) in methylene chloride (10 mL) containing triethylamine (0.28 mL, 2 mmol) was added to a solution of isobutyl chloroformate (0.2 mL, 2 mmol) in methylene chloride (10 mL) at a temperature between −78° and −65° C. After 30 minutes, a solution of 4[4-(N,N-dimethylsulfamoyl)piperizino]-2-hydroxymethylpyrimidine in methylene chloride (5 mL) was added to the reaction mixture. The reaction was allowed to warm to room temperature, stirred for 2 hours and then quenched with water (20 mL). The methylene chloride layer was collected and was washed succesively with 5% sodium bicarbonate solution and water. The organic layer was dried, evaporated and the residue was chromatographed over silica gel. Elution with a solution of methylene chloride in methanol (95:5) and evaporation of the eluent gave the title compound (0.35 g). M. P. 97°–99° C.

We claim:

1. A compound of the formula

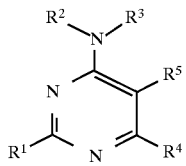

IA wherein $R^1$ is $(C_1-C_6)$alkoxycarbonyl-$(C_1-C_6)$alkyl, $(C_1-C_6)$alkyl-S—$(C_1-C_6)$alkyl,$(C_1-C_6)$alkyl—SO—$(C_1-C_6)$alkyl, $(C_1-C_6)$alkyl-$SO_2$—$(C_1-C_6)$alkyl, dihydroxy-$(C_1-C_6)$alkyl, aryl, heteroaryl, heteroaryl-$(C_1-C_6)$alkyl, aryl-$(C_1-C_6)$alkyl, $(C_1-C_6)$alkoxycarbonylaryl, aryl-$(C_1-C_6)$alkyloxy or heteroaryl-$(C_1-C_6)$alkyloxy, wherein said aryl and the aryl moieties of said aryl-$(C_1-C_6)$alkyl, $(C_1-C_6)$alkoxycarbonylaryl, and aryl-$(C_1-C_6)$alkyloxy are independently selected from phenyl and naphthyl, and wherein said heteroaryl and the heteroaryl moieties of said heteroaryl-$(C_1-C_6)$alkyl and heteroaryl-$(C_1-C_6)$alkyloxy are independently selected from wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-$(C_1-C_6)$alkyl, aryl-$(C_1-C_6)$alkyl, $(C_1-C_6)$alkoxycarbonylaryl, aryl-$(C_1-C_6)$alkyloxy and heteroaryl-$(C_1-C_6)$alkyloxy may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl, hydroxy-$(C_1-C_6)$alkyl and trifluoromethyl;

or $R^1$ is a group of the formula

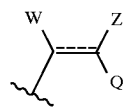

wherein the dotted line represents an optional double bond, W, Q and Z are independently selected from hydrogen, $(C_1-C_6)$alkyl and trifluoromethyl, phenyl, furyl, triazolyl, thiazolyl and thienyl, wherein said phenyl, furyl, triazolyl, thiazolyl and thienyl may optionally be substituted with one or more substituents, preferably with from zero to two substituents, independently selected from $(C_1-C_6)$alkyl, $(C_1-C_6)$alkoxy, trifluoromethyl and hydroxy;

or $R^1$ is a group of the formula

wherein $R^6$ is hydrogen, $(C_1-C_6)$alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents, preferably with from zero to two substituents, independently selected from chloro, bromo, nitro, trifluoromethyl, $(C_1-C_6)$alkoxy, —S—$(C_1-C_6)$alkyl, —SO—$(C_1-C_6)$alkyl and —$SO_2$—$(C_1-C_6)$alkyl;

or $R^1$ is a group of the formula

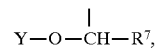

wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents, preferably with from zero to two substituents, independently selected from chloro, bromo, nitro, trifluoromethyl, $(C_1-C_6)$alkyl, $(C_1-C_6)$alkoxy, —S—$(C_1-C_6)$alkyl, —SO—$(C_1-C_6)$alkyl and —$SO_2$—$(C_1-C_6)$alkyl;

$R^2$ and $R^3$ are independently selected from hydrogen, $(C_1-C_6)$alkyl, phenyl and phenyl-$(C_1-C_4)$alkyl, wherein said phenyl and the phenyl moiety of said phenyl -$(C_1-C_4)$alkyl may optionally be substituted with one or more substituents independently selected from $(C_1-C_6)$alkyl, $(C_1-C_6)$alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents, independently selected from $(C_1-C_6)$alkyl, —$CONH_2$, —$SO_2NH_2$, N—$(C_1-C_4)$alkylsulfamoyl, N,N-di-$(C_1-C_4)$alkylsulfamoyl, $(C_1-C_6)$alkoxycarbonyl, N,N-di-$(C_1-C_4)$alkylcarbamoyl, N—$(C_1-C_4)$-alkylcarbamoyl, N-phenylcarbamoyl, $(C_1-C_6)$alkylcarbonyl, phenylcarbonyl, $(C_1-C_6)$alkylsulfonyl, $(C_1-C_6)$alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents, independently selected from $(C_1-C_4)$alkyl, $(C_1-C_4)$alkoxy, chloro, bromo, nitro, amino, cyano and trifluoromethyl;

$R^4$ is hydrogen, chloro, bromo, cyano, nitro, trifluoromethyl, amino, $(C_1-C_6)$alkyl, $(C_1-C_6)$hydroxyalkyl, $(C_1-C_6)$alkoxy, phenyl, naphthyl or furyl, wherein said phenyl, naphthyl and furyl may optionally be substituted with one or more substituents, independently selected from chloro, bromo, trifluoromethyl, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl and hydroxy; and $R^5$ is hydrogen, $(C_1-C_6)$alkyl, $(C_1-C_6)$alkoxy, trifluoromethyl, $(C_1-C_6)$hydroxyalkyl, —S—$(C_1-C_6)$alkyl, —SO—$(C_1-C_6)$alkyl, —$SO_2$—$(C_1-C_6)$alkyl, phenyl or furyl, wherein said phenyl and furyl may optionally be substituted with one or more substituents, independently selected from chloro, bromo, trifluoromethyl, $(C_1-C_6)$alkyl, $(C_1-C_6)$alkoxy, —SO—$(C_1-C_6)$alkyl, —$SO_2$—$(C_1-C_6)$alkyl and hydroxy;

or a pharmaceutically acceptable salt of such compound.

2. A method of: (a) inhibiting the enzyme sorbitol dehydrogenase in a mammal; (b) lowering the level of fructose in one or more of the tissues of a mammal that are affected by diabetes; or (c) treating or preventing a diabetic complication in a mammal; comprising administering to said mammal an amount of a compound of the formula

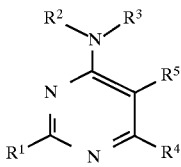

I wherein $R^1$ is hydrogen, $CF_3$, $(C_1-C_6)$alkyl, $(C_1-C_6)$alkyl-S—$(C_1-C_6)$alkyl, $(C_1-C_6)$alkyl-SO—$(C_1-C_6)$alkyl, $(C_1C_6)$alkyl-$SO_2$—$(C_1-C_6)$alkyl, hydroxy-$(C_1-C_6)$alkyl, dihydroxy-$(C_1-C_6)$alkyl, $(C_1-C_6)$alkoxy, $(C_1-C_6)$ alkoxycarbonyl-$(C_1-C_6)$alkyl, aryl selected from phenyl and naphthyl, aryl-$(C_1-C_6)$alkyl wherein the aryl moiety is selected from phenyl and naphthyl, $(C_1-C_6)$ alkoxycarbonylaryl wherein the aryl moiety is selected from phenyl and naphthyl, aryl-$(C_1-C_6)$alkyl wherein the aryl moiety is selected from phenyl and naphthyl, aryl-$(C_1-C_6)$ alkyloxy wherein the aryl moiety is selected from phenyl and napthyl, heteroaryl selected from pyridyl, furyl, tetrahydrofuryl, thienyl, imidazolyl, pyrazolyl, triazolyl, thiazolyl, oxazolyl, benzothiazolyl, benzofuranyl, and benzothienyl; heteroaryl-$(C_1-C_6)$alkyl wherein heteroaryl is defined as above, or heteroaryl-$(C_1-C_6)$alkyloxy wherein heteroaryl is defined as above, and wherein said aryl and heteroaryl groups, the aryl moieties of said aryl-$(C_1-C_6)$ alkyl, $(C_1-C_6)$alkoxycarbonylaryl and aryl-$(C_1-C_6)$ alkyloxy and the heteroaryl moiety of said heteroaryl-$(C_1-C_6)$alkyl may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl, hydroxy-$(C_1-C_6)$alkyl and trifluoromethyl;

or $R^1$ is a group of the formula

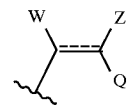

wherein the dotted line represents an optional double bond, W, Q and Z are independently selected from hydrogen, $(C_1-C_6)$alkyl and trifluoromethyl, phenyl, furyl, triazolyl, thiazolyl and thienyl, wherein said phenyl, furyl, triazolyl, thiazolyl and thienyl may optionally be substituted with one or more substituents independently selected from $(C_1-C_6)$ alkyl, $(C_1-C_6)$alkoxy, trifluoromethyl and hydroxy;

or $R^1$ is a group of the formula

wherein $R^6$ is hydrogen, $(C_1-C_6)$alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents independently selected from chloro, bromo, nitro, trifluoromethyl, $(C_1-C_6)$ alkoxy, —S—$(C_1-C_6)$alkyl, —SO—$(C_1-C_6)$alkyl and —$SO_2$—$(C_1-C_6)$alkyl;

or $R^1$ is a group of the formula

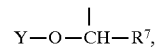

wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —$SO_2$—$(C_1-C_6)$alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents independently selected from chloro, bromo, nitro, trifluoromethyl, $(C_1-C_6)$alkyl, $(C_1-C_6)$alkoxy, —S—$(C_1-C_6)$alkyl, —SO—$(C_1-C_6)$alkyl and —$SO_2$—$(C_1-C_6)$alkyl;

$R^2$ and $R^3$ are independently selected from hydrogen, $(C_1-C_6)$alkyl, phenyl and phenyl-$(C_1-C_4)$alkyl, wherein said phenyl and the phenyl moiety of said phenyl —$(C_1-C_4)$alkyl may optionally be substituted with one or more substituents independently selected from $(C_1-C_6)$alkyl, $(C_1-C_6)$alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents, independently selected from $(C_1-C_6)$alkyl, —$CONH_2$, —$SO_2NH_2$, N—$(C_1-C_4)$alkylsulfamoyl, N,N-di-$(C_1-C_4)$alkylsulfamoyl, $(C_1-C_6)$alkoxycarbonyl, N,N-di-$(C_1-C_4)$alkylcarbamoyl, N—$(C_1-C_4)$ alkylcarbamoyl, N-phenylcarbamoyl, $(C_1-C_6)$ alkylcarbonyl, phenylcarbonyl, $(C_1-C_6)$alkylsulfonyl, $(C_1-C_6)$alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents independently selected from $(C_1-C_4)$alkyl, $(C_1-C_4)$alkoxy, chloro, bromo, nitro, amino, cyano and trifluoromethyl;

$R^4$ is hydrogen, chloro, bromo, cyano, nitro, trifluoromethyl, amino, $(C_1-C_6)$alkyl, $(C_1-C_6)$hydroxyalkyl, $(C_1-C_6)$alkoxy, phenyl, naphthyl or furyl, wherein said phenyl, naphthyl and furyl may optionally be substituted with one or more substituents independently selected from chloro, bromo, trifluoromethyl, $(C_1-C_6)$alkyl, $(C_1-C_6)$alkoxy, —S—$(C_1-C_6)$alkyl, —SO—$(C_1-C_6)$alkyl and hydroxy; and $R^5$ is hydrogen, $(C_1-C_6)$alkyl, $(C_1-C_6)$alkoxy, trifluoromethyl, $(C_1-C_6)$hydroxyalkyl, —S—$(C_1-C_6)$alkyl, —SO—$(C_1-C_6)$alkyl, -SO$_2$—$(C_1-C_6)$alkyl, phenyl or furyl, wherein said phenyl and furyl may optionally be substituted with one or more substituents independently selected from chloro, bromo, trifluoromethyl, $(C_1-C_6)$alkyl, $(C_1-C_6)$alkoxy, —SO—$(C_1-C_6)$alkyl, —SO$_2$—$(C_1-C_6)$alkyl and hydroxy;

or a pharmaceutically acceptable salt thereof, effective in, respectively: (a) inhibiting the enzyme sorbitol dehydrogenase; (b) lowering the level of fructose in one or more of the tissues of a mammal that are affected by diabetes; or (c) treating or preventing a diabetic complication.

3. A method according to claim 2, wherein the compound of formula I that is employed is a compound wherein $R^1$ is $(C_1-C_6)$alkoxycarbonyl-$(C_1-C_6)$alkyl, $(C_1-C_6)$alkyl-S—$(C_1-C_6)$alkyl, $(C_1-C_6)$alkyl-SO—$(C_1-C_6)$alkyl, $(C_1-C_6)$alkyl-SO$_2$—$(C_1-C_6)$alkyl, dihydroxy-$(C_1-C_6)$alkyl, aryl, heteroaryl, heteroaryl-$(C_1-C_6)$alkyl, aryl-$(C_1-C_6)$alkyl, $(C_1-C_6)$alkoxycarbonylaryl, aryl-$(C_1-C_6)$alkyloxy or heteroaryl-$(C_1-C_6)$alkyloxy, wherein said aryl and the aryl moieties of said aryl-$(C_1-C_6)$alkyl, $(C_1-C_6)$alkoxycarbonylaryl, and aryl-$(C_1-C_6)$alkyloxy are independently selected from phenyl and naphthyl, and wherein said heteroaryl and the heteroaryl moieties of said heteroaryl-$(C_1-C_6)$alkyl and heteroaryl-$(C_1-C_6)$alkyloxy are independently selected from wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-$(C_1-C_6)$alkyl, aryl-$(C_1-C_6)$alkyl, $(C_1-C_6)$alkoxycarbonylaryl, aryl-$(C_1-C_6)$alkyloxy and heteroaryl-$(C_1-C_6)$alkyloxy may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl, hydroxy-$(C_1-C_6)$alkyl and trifluoromethyl.

4. A method according to claim 2 of inhibiting sorbitol dehydrogenase in a mammal.

5. A method according to claim 2 of lowering the level of fructose in one or more of the tissues of a mammal that are affected by diabetes.

6. A method according to claim 2 of treating or preventing a diabetic complication in a mammal.

7. A method according to claim 5, wherein said diabetic complication is diabetic neuropathy, a diabetic vascular disease, microangiopathy or diabetic macroangiopathy.

8. A mutual prodrug of a compound according to claim 1 and an aldose reductase inhibiting compound.

9. A mutual prodrug of a compound of the formula I, as defined in claim 2, or a pharmaceutically acceptable salt thereof, and an aldose reductase inhibiting compound.

10. A method of: (a) inhibiting the enzyme sorbitol dehydrogenase in a mammal; (b) lowering the level of fructose in one or more of the tissues of a mammal that are affected by diabetes; or (c) treating or preventing a diabetic complication in a mammal; comprising administering to said mammal an amount of a mutual prodrug of a compound according to claim 1 and an aldose reductase inhibiting compound, or a pharmaceutically acceptable salt of such a prodrug, that is effective in, respectively: (a) inhibiting the enzyme sorbitol dehydrogenase, (b) lowering the level of fructose in one or more of the tissues of a mammal that are affected by diabetes, or (c) treating or preventing a diabetic complication in a mammal.

11. A method of: (a) inhibiting the enzyme sorbitol dehydrogenase in a mammal; (b) lowering the level of fructose in one or more of the tissues of a mammal that are affected by diabetes; or (c) treating or preventing a diabetic complication in a mammal; comprising administering to said mammal an amount of a mutual prodrug of an aldose reductase inhibiting compound and a compound of the formula I, as defined in claim 1, or a pharmaceutically acceptable salt of such a prodrug, that is effective in, respectively: (a) inhibiting the enzyme sorbitol dehydrogenase, (b) lowering the level of fructose in one or more of the tissues of a mammal that are affected by diabetes, or (c) treating or preventing a diabetic complication in a mammal.

12. A method of lowering the level of fructose in one or more of the tissues of a mammal that are affected by diabetes, comprising administering to said mammal a fructose lowering effective amount of a compound of the formula I, as defined in claim 1, or a pharmaceutically acceptable salt thereof, in combination with a fructose lowering effective amount of an aldose reductase inhibiting compound, or a pharmaceutically acceptable salt thereof.

13. A method of treating or preventing a diabetic complication such as diabetic neuropathy, diabetic retinopathy, diabetic nephropathy, or diabetic microangiopathy or macroangiopathy in a mammal, comprising administering to said mammal an amount of a compound of the formula I, as defined in claim 1, or a pharmaceutically acceptable salt thereof, effective in treating or preventing such complication, in combination with an amount of an aldose reductase inhibiting compound, or a pharmaceutically acceptable salt thereof, effective in treating or preventing such complication.

14. A method of lowering the level of fructose in one or more of the tissues of a mammal that are affected by diabetes, comprising administering to said mammal a fructose lowering effective amount of a compound of the formula I, as defined in claim 1, or a pharmaceutically acceptable salt thereof.

15. A method of treating or preventing a diabetic complication such as diabetic neuropathy, diabetic retinopathy, diabetic nephropathy, or diabetic microangiopathy or macroangiopathy in a mammal, comprising administering to said mammal an amount of a compound of the formula I, as defined in claim 1, or a pharmaceutically acceptable salt thereof, effective in treating or preventing such complication.

16. A method according to claim,14, wherein the compound of formula I, or pharmaceutically acceptable salt thereof, that is employed, is a compound wherein $R^1$ is $(C_1-C_6)$alkoxycarbonyl-$(C_1-C_6)$alkyl, $(C_1-C_6)$alkyl-S—$(C_1-C_6)$alkyl, $(C_1-C_6)$alkyl-SO—$(C_1-C_6)$alkyl, $(C_1-C_6)$alkyl-SO$_2$—$(C_1-C_6)$alkyl,dihydroxy-$(C_1-C_6)$alkyl, aryl, heteroaryl, heteroaryl-$(C_1-C_6)$alkyl, aryl-$(C_1-C_6)$alkyl, $(C_1-C_6)$alkoxycarbonylaryl, aryl-$(C_1-C_6)$alkyloxy or heteroaryl-$(C_1-C_6)$alkyloxy, wherein said aryl and the aryl moieties of said aryl-$(C_1-C_6)$alkyl, $(C_1-C_6)$alkoxycarbonylaryl, and aryl-$(C_1-C_6)$alkyloxy are independently selected from phenyl and naphthyl, and wherein said heteroaryl and the heteroaryl moieties of said heteroaryl-$(C_1-C_6)$alkyl and heteroaryl-$(C_1-C_6)$alkyloxy are independently selected from wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-$(C_1-C_6)$alkyl, aryl-$(C_1-C_6)$alkyl, $(C_1-C_6)$alkoxycarbonylaryl, aryl-$(C_1-C_6)$alkyloxy and heteroaryl-$(C_1-C_6)$alkyloxy may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl, hydroxy-$(C_1-C_6)$alkyl and trifluoromethyl.

17. A method according to claim 15, wherein the compound of formula I, or pharmaceutically acceptable salt thereof, that is employed, is a compound wherein $R^1$ is $(C_1-C_6)$alkoxycarbonyl-$(C_1-C_6)$alkyl, $(C_1-C_6)$alkyl-S—$(C_1-C_6)$alkyl, $(C_1-C_6)$alkyl-SO—$(C_1-C_6)$alkyl, $(C_1-C_6)$alkyl-SO$_2$—$(C_1-C_6)$alkyl, dihydroxy-$(C_1-C_6)$alkyl, aryl, heteroaryl, heteroaryl-$(C_1-C_6)$alkyl, aryl-$(C_1-C_6)$alkyl, $(C_1-C_6)$alkoxycarbonylaryl, aryl-$(C_1-C_6)$alkyloxy or heteroaryl-$(C_1-C_6)$alkyloxy, wherein said aryl and the aryl moieties of said aryl-$(C_1-C_6)$alkyl, $(C_1-C_6)$alkoxycarbonylaryl, and aryl-$(C_1-C_6)$alkyloxy are independently selected from phenyl and naphthyl, and wherein said heteroaryl and the heteroaryl moieties of said heteroaryl-$(C_1-C_6)$alkyl and heteroaryl-$(C_1-C_6)$alkyloxy are independently selected from wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-$(C_1-C_6)$alkyl, aryl-$(C_1-C_6)$alkyl, $(C_1-C_6)$alkoxycarbonylaryl, aryl-$(C_1-C_6)$alkyloxy and heteroaryl-$(C_1-C_6)$alkyloxy may optionally be substituted with one or more substituents independently selected from chloro, bromo, $(C_1-C_6)$alkyl, $(C_1-C_6)$alkoxy, —S—$(C_1-C_6)$alkyl, —SO—$(C_1-C_6)$alkyl, —SO$_2$—$(C_1-C_6)$alkyl, hydroxy-$(C_1-C_6)$alkyl and trifluoromethyl.

18. A pharmaceutical composition for treating or preventing a disorder or condition that can be treated or prevented by inhibiting the enzyme sorbitol dehydrogenase in a mammal, comprising, a sorbitol dehydrogenase inhibiting effective amount of a sorbitol dehydrogenase inhibitor or a pharmaceutically acceptable salt thereof; and a pharmaceutically acceptable carrier.

19. A pharmaceutical composition for treating or preventing a disorder or condition that can be treated or prevented by inhibiting the enzyme sorbitol dehydrogenase in a mammal, comprising:

a) a sorbitol dehydrogenase inhibitor or a pharmaceutically acceptable salt thereof; and b) an aldose reductase inhibitor or a pharmaceutically acceptable salt thereof; and c) a pharmaceutically acceptable carrier;

wherein the amounts of the active compounds are such that the combination is effective in treating or preventing such disorder or condition.

20. A method for treating or preventing a disorder or condition that can be treated or prevented by inhibiting the enzyme sorbitol dehydrogenase in a mammal, comprising administering to said mammal requiring such treatment or prevention a sorbitol dehydrogenase inhibiting effective amount of a sorbitol dehydrogenase inhibitor or a pharmaceutically acceptable salt thereof.

21. A method for treating or preventing a disorder or condition that can be treated or prevented by inhibiting the enzyme sorbitol dehydrogenase in a mammal, comprising administering to said mammal requiring such treatment or prevention:

a) a sorbitol dehydrogenase inhibiting effective amount of a sorbitol dehydrogenase inhibitor or a pharmaceutically acceptable salt thereof; and b) an aldose reductase inhibiting effective amount of an aldose reductase inhibitor or a pharmaceutically acceptable salt thereof;

wherein the amounts of the active compounds are such that the combination is effective in treating or preventing such disorder or condition.

* * * * *